United States Patent [19]
Horlick et al.

[11] Patent Number: 5,976,807
[45] Date of Patent: Nov. 2, 1999

[54] EUKARYOTIC CELLS STABLY EXPRESSING GENES FROM MULTIPLE TRANSFECTED EPISOMES

[75] Inventors: Robert A. Horlick, Plainsboro; Bassam B. Damaj, Lawrenceville, both of N.J.; Alan K. Robbins, Wilmington, Del.

[73] Assignee: Pharmacopeia, Inc., Cranbury, N.J.

[21] Appl. No.: 09/130,114

[22] Filed: Aug. 6, 1998

Related U.S. Application Data

[63] Continuation-in-part of application No. 09/040,961, Mar. 18, 1998.
[51] Int. Cl.⁶ ...................................................... C12Q 1/68
[52] U.S. Cl. .................................. 435/6; 435/369; 435/467
[58] Field of Search ................................. 435/6, 369, 467

[56] References Cited

PUBLICATIONS

Horlick et al., *Prot. Expr. and Purif.*, vol. 9, 1977, pp. 301–308, 1997.

*Primary Examiner*—James Ketter
*Attorney, Agent, or Firm*—Darby & Darby

[57] ABSTRACT

A method is described for producing recombinant eukaryotic cell lines expressing multiple proteins of interest. Eukaryotic host cells are transfected with (a) a first episome which contains an EBV origin of replication and a first gene encoding a protein of interest; and (b) a second episome containing an EBV origin of replication and a second gene encoding a protein of interest. Transfected cells are obtained expressing an EBNA 1 protein. The cells are grown under conditions wherein the episomes express the first and second genes.

26 Claims, 25 Drawing Sheets

FIG. 1A

```
TCGCGGCGTTTCGGTGATGACGTTGAAAACCTTCTGACACATGCAGCTCACAGCTTGTCTGTAAGCGGAT
GCCGGGAGCAGACAAGCCCGTCAGGCGCGTTGGCGGGTGTTGGCGGGTCGGGGGCTGGCTTAACTATGCGGCATCAGA
GCAGATTGTACTGAGAGTGCACCATATGCGGTGTGAAATACCGCACAGATGCGTAAGGAGAAAATACCGCATCAGGCGCC
ATTCGCCATTCAGGCTGCCGCAACTGTTGGGAAGGGCGATCGGTGCGGGCCTCTTCGCTATTACGCCAGCTGGCGAAAGG
GGATGTGCTGCAAGGCGATTAAGTTGGGTAACGCCAGGGTTTTCCCAGTCACGACGTTGTAAAACGACGGCCAGTGCCAA
GCTTGCATGCCTGCAGGTCGACTGGGGATTATTCTTTAGTGCGGGGAATACACGCGTTTAATACGATTGAGGGCGTC
TCCTAACAAG
TTACATCACTCCTGCCCTTCCTGCCCTTCCTCACCCTCTCATCTCCATCACCTCCTTCATCTCCGTCATCACCT
CCTCCGCGGCAGCCCCTTCCACCATAGGTGGAAACCAGGAGGCAATCTACTCCATCGTCAAAGCTGCACACAGTCACC
CTGATATTGCAGTAGGAGCGGGCTTTGTCATAAGGTCCTCATCCTTCAAACCTCAGCAAGTCTCAGCAAATATGAGT
TTGTAAAAGACGAGCTCAATGGTTGTAAGACGACATTGTGAAAGCACAAGGGCAGTTCCTGCCTTAGTTGTAAGGGAGTC
AGGGGAGACGACTCCATATACGAACACACGGCGACCCAAGTTCCTTCGTCGTAGTCCTTCTACGTGACTCCTAGCCAGGAG
TTACTACCTTCCATATACGAACACACGGCGACCCAAGTTCCTTCGTCGTAGTCCTTCTACGTGACTCCTAGCCAGGAG
AGCTCTTAAACCTTCTGCAATGTTCTCAAATTTCGGGTTGGAACCTCTTGGGGCCTTCAGTGCTTCCCTTTCCAAACCACCCTCTT
TTTTGCGCCTGCCTCCATCACCCTGACCCCGGGGTCCAGTGCTCAGCCTTCTCTGGGCCTTCATCTGCGGGCCCTGCTCT
ATCGCTCCGGGGCACGTCAGCTCACCATCTGGGCACCATCTGGGTATTCAAATAATCGGCTTCCCCTACAGG
GTGGAAAAATGGCCTTCTACCTGAGGGGGCCTGCGGCGGTGAGACCCGGATGATGATGACTACTGGGACTCCTGG
GCCTCTTTCTCCACGTCCACGACCTCTGACGACCTCTGACCCCGGCCTTTCTTCACGTCCTTCTACCC
CGGCGGCCGGCTCCACTACCTCCTGACCCCTGCCCCCTCCTGCCCTGGCCCTGCCCCCTCCTGCCCCTCCTGACCCCGGCC
TCCACCTCCTGCCCCTCCTGCCCCCCTCCTGCCCCTCCTGCCCCCTCCTGCCCCCTCCTGCCCCCTC
CTGCCCCTCCTGCCCCTCCTGCCCCTCCTGCCCCTCCTGCCCCTCCTGCCCCTCCTGCCCCTCCTGCC
CCTCCTGCCCCTCCTGCCCCTCCTGCCCCTCCTGCCCCTCCTGCCCCTCCTGCCCCTCCTGCCCCTCCTC
TGCTCCTGCCCCTCCTGCCCCTCCTGCCCCTCCTGCCCCTCCTGCCCCTCCTGCCCCTCCTGCCCCTCCTC
CTGCTCCTGCCCCTCCTGCCCCTCCTGCCCCTCCTGCCCCTCCTGCCCCTCCTGCCCCTCCTGCCCCCT
CCTGCCCCTCCTGCCCCTCCTGCCCCTCCTGCCCCTCCTGCCCCTCCTGCCCCTCCTGCCCCTCCCC
TCCTGCCCCTCCTGCCCCTCCTGCCCCTCCTGCCCCTCCTGCCCCTCCTGCCCCTCCTGCCCCTCCTGCCC
```

FIG. 1B

```
CTCCTGCCCCCTCCTGCCCCCTCCTGCTCCTGCCCCCTCCTGCTCCTGCCCCCTCCTGCC
CCTCCTGCTCCTGCCCCCTCCTGCTCCTGCCCCCTCCTGCTCCTGCCCCCTCCTGTTCC
ACCGTGGTCCCTTTGCAGCCAATGCAACTTGGACGTTTTGGGGTCTCCGACACCATCTCTATGTCTTGGCCCTGATC
CTGAGCCGCCCGGGGCTTCCTGGTCTTCCGCTCGTCCTCGTCCTTCCCGTCCTCGTCCATGGTTATCACCCCCT
CTTCTTTGAGGTCCACTGCCGCCCGGAGCCTTCTGTGTCCAGATGTGTCTCCTCTCCTAGGCCATTTCCAGGTCCTGT
ACCTGGCCCCTCGTCAGACAT
GATTCACACTAAAGAGATCCCCGGGTACCCGGGGATCCTCTAGAGTCAGGCTGATCG
GTCCCGGTGTCTTCTATGGAGGTCAAAACAGCGTGGATGGCGTCTCCAGGCGATCTGACGGTTCACTAAACGAGCTCTGC
TTATATAGACCTCCACCGTACACGCCTACCGCCATTTGCGTCACGCCCATTGACGTGAAATCTGACGTTGTTACGACATTTGGAAAGTCC
CGTTGATTTTGGTGCCAAAACAAACTCCCATTGACGTCAATGGGGTGGAGACTTGGAAATCCCCGTGAGTCAAACCGCTA
TCCACGCCCATTGATGTACTGCCAAAACGCCATCACCATGGTAATAGCGATGACTAATACGTAGATGTACTGCCAAGTAG
GAAAGTCCCATAAGGTCATGTACTGCCAAGCGCATAATGCCAGGCGCAGTTACCGTCATTGACGTCAATAGGGGCGTACTT
GGCATATGATACACTTGATGTACTGCCAAGTGGGCAGTTTACCGTCAATGGGCCAGTCCACCCATTGACGTCAATGAAAGTCCC
TATTGGCGTTACTATGGGAACATACGTCATTATGGGAACTCCATATATGTGGACATAGCTGTTCCTGTGTGAAATTGTTATCCGCTCACAATTCCACACA
TTACCGTAAGTTATGTAACGCGGAACTCCATATATGTGGACATAGCTGTTCCTGTGTGAAATTGTTATCCGCTCACAATTCCACACA
GTCAATAATCAATGGGCAAGCTTGGCTAATCATGTGAAAGTGTAAAGCCTGGGGTGCCTAATGAGTGAGCTAACTCACATTAATTGCGTTGCGCTCA
ATGCAATGAGCAACGTTGGCCAAGCATAAAGTGTAAAGCCTGGGGTGCCTAATGAGTGAGCTAACTCACATTAATTGCGTTGCGCTCA
ACATACGAGCCGGAAGCATAAAGTGTAAAGCCTGGGGTGCCTAATGAGTGAGCTAACTCGCGCGGGAGAGGCGGTTTGCG
CTGCCCGCTTCCAGTCGGGAAACCTGTCGTGCCAGCTGCATTAATGAATCGGCCAACGCGCGGGGAGAGGCGGTTTGCG
TATTGGGCGCTCTTCCGCTTCCTCGCTCACTGACTCGCTGCGCTCGGTCGTTCGGCTGCGGCGAGCGGTATCAGCTCACT
CAAAGGCGGTAATACGGTTATCCACAGAATCAGGGGATAACGCAGGAAAGAACATGTGAGCAAAAGGCCAGCAAAAGGCC
AGGAACCGTAAAAAGGCCGCGTTGCTGGCGTTTTTCCATAGGCTCCGCCCCCCTGACGAGCATCACAAAAATCGACGCTC
AAGTCAGAGGTGGCGAAACCCGACAGGACTATAAAGATACCAGGCGTTTCCCCCTGGAAGCTCCCTCGTGCGCTCTCCTG
TTCCGACCCTGCCGCTTACCGGATACCTGTCCGCCTTTCTCCCTTCGGGAAGCGTGGCGCTTTCTCATAGCTCACGCTGT
AGGTATCTCAGTTCGGTGTAGGTCGTTCGCTCCAAGCTGGGCTGTGTGCACGAACCCCCCGTTCAGCCCGACCGCTGCGC
CTTATCCGGTAACTATCGTCTTGAGTCCAACCCGGTAAGACACGACTTATCGCCACTGGCAGCAGCCACTGGTAACAGGA
TTAGCAGAGCGAGGTATGTAGGCGGTGCTACAGAGTTCTTGAAGTGGTGGCCTAACTACGGCTACACTAGAAGGACAGTA
TTTGGTATCTGCGCTCTGCTGAAGCCAGTTACCTTCGGAAAAAGAGTTGGTAGCTCTTGATCCGGCAAACAAACCACCGC
TGGTAGCGGTGGTTTTTTTGTTTGCAAGCAGCAGATTACGCGCAGAAAAAAAGGATCTCAAGAAGATCCTTTGATCTTTT
```

CTACGGGGTCTGACGCTCAGTGGAACGAAAACTCACGTTAAGGGATTTTGGTCATGAGATTATCAAAAAGGATCTTCACC
TAGATCCTTTTAAATTAAAATGAAGTTTAAATCAATCTAAATGAAGTATATAGAGTAAACTTGGTCTGACAGTTACCAATG
CTTAATCAGTGAGGCACCTATCTCAGCGATCTGTTCATTCGTTCTATTCCATAGTTGCCTGACTCCCGTCGTGTAGATAA
CTACGATACGGGAGGGCTTACCATCTGGCCCCAGTGCTGCAATGATACCGCGAGACCACGCTCACCGGCTCCAGATTTA
TCAGCAATAAACCAGCAGCCGGAAGGGCCGAGCGCAGAAGTGGTCCTGCAACTTTATCCGCCTCCATCCAGTCTATTAA
TTGTTGCCGGGAAGCTAGAGTAAGTAGTTCGCCAGTAATTACGCAACGTTGTTGCCATTGCTACAGGCATCGTGG
TGTCACGCTCGTCGTTTGGTATGGCTTCAGCTCCGGTTCCCAACGATCAAGGCGAGTTACATGATCCCCATGTTG
TGCAAAAAGCGGTTAGCTCCTTCGGTCGTCATGCCATCCGTAAGATGCTTTTCTGTGACTGGTGAGTACTCAACCAAGTCAT
GGCAGCACTGCATAATTCTCTTACTGTCGGGCGACCGAGTTGCTCTTGCCCGGTCAATACGGGATAATACCGCGCCACATAGCAGAACT
TCTGAGAATAGTGTATGCGGCGACCGAGTTGCTCTTGCCCGGTCAAACTCTCAAGGATCTTACCGCTGTTGAGATCCAGTTCGAT
TTAAAAGTGCTCATCATTGGAAAACGTTCTTCGGGGCGAAAACTCTCAAGGATCTTACCGCTGTTGAGATCCAGTTCGAT
GTAACCCACTCGTGCACCCAACTGATCTTCAGCATCTTTTACTTTCACCAGCGTTTCTGGGTGAGCAAAAACAGGAAGGC
AAAATGCCGCAAAAAAGGGAATAAGGGCGACACGGAAATGTTGAATACTCATACTCTTCCTTTTCAATATTATTGAAGC
ATTTATCAGGGTTATTGTCTCATGAGCGGATACATATTTGAATAGTATTTAGAAAAATAAACAAATAGGGGTTCCGCGCAC
ATTTCCCCGAAAAGTGCCACCTGACGTCTAAGAAACCATTATTATCATGACATTAACCTATAAAAATAGGCGTATCACGA
GGCCCTTTCGTC

FIG. 2A

```
ATGTCTGACGAGGGGCCAGGTACAGGACCTGGAAATGGCCTAGGAGAGAAGGGAGACACATCTGGACCAGAAGGCTCCGGCGGCAGTGGACCTCAAAGAA
         +         +         +         +         +         +         +         +         +         +   100
TACAGACTGCTCCCGGTCCCCATGTCCTGGACCTTTACCGGATCCTCTCTTCCCTCTGTAGACCTGGTCTTTCCAGGCCCGTCACCTGGAGTTTCTT
 M  S  D  E  G  P  G  T  G  P  G  N  G  L  E  K  G  D  T  S  G  P  E  G  S  G  G  S  G  P  Q  R

GAGGGGGTGATAACCATGGACGAGGACGGGAAGGACGAGGACGAGGAGGACCAGGAGAGCCGAGTCCTTCTGCTCCTCCGCCTTCGTCCTGCTGTCGAGGATCAGGGCCAAGACATAG
         +         +         +         +         +         +         +         +         +         +   200
CTCCCCACTATTGGTACCTGCTCCTGCCCCTTCCTGCTCCTGCTGCTCCTCGGCTCAGGAAGACGAGGAGGCGGAAGGCGGAAGCAGGACGAGGCCTAGTCCCGGTTCTGTATC
 R  G  G  D  N  H  G  R  G  R  G  R  G  R  G  R  G  R  P  G  A  P  G  G  S  G  S  G  P  R  H  R

AGATGGTGTCCGGAGACCCCAAAAACGTCCAAGTTGCATTGGCTGCAAAGGGACCCACGGTGAACAGGACCAGGAGCAGGGCCAGGAGCA
         +         +         +         +         +         +         +         +         +         +   300
TCTACCACAGGCCTCTGGGGTTTTTGCAGGTTCAACGTAACCGACGTTTCCCTGGTGCCACCTTGTCCTGGTCCTCGTCCCGGTCCTCGT
 D  G  V  R  R  P  Q  K  R  P  S  C  I  G  C  K  G  T  H  G  G  T  G  A  G  A  G  G  A  G  A

GGAGGGGCAGGAGCAGGAGCAGGGGCAGGAGCAGGAGCAGGGGCAGGAGCAGGAGCAGGGGCAGGAGCAGGAGCAGGGGCAGGAGCAGGAGCAGGGGCAGGAGCAGGAG
         +         +         +         +         +         +         +         +         +         +   400
CCTCCCCGTCCTCGTCCTCGTCCCCGTCCTCGTCCTCGTCCCCGTCCTCGTCCTCGTCCCCGTCCTCGTCCTCGTCCCCGTCCTCGTCCTC
 G  E  A  G  G  A  G  G  A  G  A  G  G  A  G  G  A  G  A  G  G  A  G  G  A  G  A  G  G  A  G

GAGGGGCAGGAGCAGGAGCAGGGGCAGGAGCAGGAGCAGGGGCAGGAGCAGGAGCAGGGGCAGGAGCAGGAGCAGGGGCAGGAGCAGGAGCAGGGGCAGG
         +         +         +         +         +         +         +         +         +         +   500
CTCCCCGTCCTCGTCCTCGTCCCCGTCCTCGTCCTCGTCCCCGTCCTCGTCCTCGTCCCCGTCCTCGTCCTCGTCCCCGTCC
 G  E  A  G  G  A  G  G  A  G  A  G  G  A  G  G  A  G  A  G  G  A  G  G  A  G  A  G  G  A  G
```

FIG. 2B

```
AGGGGCAGGAGCAGGAGGGGCAGGAGCAGGAGGGGCAGGAGCAGGAGGGGCAGGAGCAGGAGGA
                                                                    600
TCCCCGTCCTCGTCCTCCCCGTCCTCGTCCTCCCCGTCCTCGTCCTCCCCGTCCTCGTCCTCCT
 G  A  G  G  G  A  G  G  A  G  G  G  A  G  G  A  G  G  G  A  G  G

GGGGCAGGAGCAGGAGGGGCAGGAGCAGGAGGGGCAGGAGCAGGAGGGGCAGGAGCAGGAG
                                                                    700
CCCCGTCCTCGTCCTCCCCGTCCTCGTCCTCCCCGTCCTCGTCCTCCCCGTCCTCGTCCTC
 G  A  G  G  A  G  G  G  A  G  G  A  G  G  G  A  G  G  A  G

GGGCAGGAGCAGGAGGGGCAGGAGCAGGAGGGGCAGGAGCAGGAGGGGCAGGAGCAGG
                                                                    800
CCCGTCCTCGTCCTCCCCGTCCTCGTCCTCCCCGTCCTCGTCCTCCCCGTCCTCGTCC
 G  A  G  G  A  G  G  G  A  G  G  A  G  G  G  A  G  G  A  G

CCCGTCCTCGTCCTCCCCGTCCTCGTCCTCCCCGTCCTCGTCCTCCCCGTCCTCGTCC

GGGCAGGAGCAGGAGGGGCAGGAGCAGGAGGGGCAGGAGCAGGAGGGGCAGGAGCAGG
 G  A  G  G  A  G  G  G  A  G  G  A  G  G  G  A  G  G  A  G

AGGGGCAGGAGCAGGAGGGGCAGGAGCAGGAGGGGCAGGAGCAGGAGGGGCAGGAGGGCA
                                                                    900
TCCCCGTCCTCGTCCTCCCCGTCCTCGTCCTCCCCGTCCTCGTCCTCCCCGTCCTCCCCGT
 G  A  G  G  A  G  G  G  A  G  G  A  G  G  G  A  G  G  A  G  G  A

GGAGGGGCAGGAGCAGGAGGGGCAGGAGGTGAGGCCGGGGTCGAGGAGGCA
                                                                    1000
CCTCCCCGTCCTCGTCCTCCCCGTCCTCCACTCCGGCCCCAGCTCCTCCGT
 G  A  G  G  G  A  G  G  A  G  G  G  A  G  G  G  R  G  G
```

FIG. 2C

```
GTGGAGGCCGGGGTCGAGGAGGTAGTGGAGGCCGCGGGTAGAGGACGTGAAAGAGCCAGGGGGAAGTCGTGA
                                                                          1100
CACCTCCGGCCCCAGTCTCCTCCATCACCTCCGGGCCCCAGCTCCCCCTTCGTCCCCCTTCAGCACT
 S  G  G  R  G  G  S  G  R  G  R  G  G  S  G  R  R  G  R  E  A  R  G  G  S  R  E
AAGAGCCAGGGGGAGAGGTCGTGGACGTGGAGAAAAGAGGCCCCAGTAGTCAGTCAGTCCCCAGGCCCCCTCCA
                                                                          1200
TTCTCGGTCCCCCTCTCCCAGCACCTGCACATCTTTTTCTCCGGGTCATCAGTCAGTCAGTCAGGGGTCCGGGGAGGT
 R  A  R  G  R  G  R  G  E  K  R  P  S  S  Q  S  S  S  S  G  S  P  P  R  R  P  P  P
GGTAGAAGGCCATTTTTTCCACCTGTAGGGAAGCCGATTATTTTGAATACCACCAAGAAGGTGGCCCAGATGTGAGCTGACGTGCCCCGGAGCGA
                                                                          1300
CCATCTTCCGGTAAAAGGGGACATCCCCTTCGGCTAATAAAACTTATGGTGTTCTTCCACCGGGTCTACCACTCGGGGTGCACGGGGCCCTCGCT
 G  R  R  P  F  F  H  P  V  G  E  A  D  Y  F  E  Y  H  Q  E  G  G  P  D  G  E  P  D  V  P  P  G  A
TAGAGCAGGGGCCCCGAGATGACCCAGGAGAAGGCCCAAGCACTGGACCCGGGTCAGGGTGATGAGGCAGGGCGCAAAAAGGAGGTGGTTTGAAAA
                                                                          1400
ATCTCGTCCCCGGGGCTCTACTGGGTCCTCTTCCGGGTTCGTGACCCTGGGGCCCAGTGCCCAGTCCCATGGGGAAGGCCCAGTCCCCACCAAACCTTT
 I  E  Q  G  P  A  D  D  P  G  E  G  P  S  T  G  P  R  G  Q  G  D  G  G  R  K  K  G  G  W  F  G  K
GCATCGTGGTCAAGGAGGTTCCAACCCGAAATTTGAGAACATTGCAGAAGGTTTAAGAGCTCTCCTGGCTAGGAGTCACGTAGAAAGGACTACCGACGAA
                                                                          1500
CGTAGCACCAGTTCCTCCAAGGTTGGGCTTTAAACTCTTGTAACGTCTTCAAATTCTGAGAGACCGATCCTCAGTGCATCTTTCCTGATGGCTGCTT
 H  R  G  Q  G  S  N  P  K  F  E  N  I  A  E  G  L  R  A  L  L  A  R  S  H  V  E  R  T  T  D  E
```

```
GCATGCAGGAAAAGGACAAGCAGCGAAAATTCACGCCCCCTTGGGAGGTGGCGGCATATGCAAAGGATAG
CACTCCCACTCTACTACTGGGTATCATATGCTGACTGTATATGCATGAGGATAGCATATGCTACCCGGAT
ACAGATTAGGATAGCATATACTACCCAGATATAGGATAGCATATGCTACCCAGATATAGATTAGG
ATAGCCTATGCTACCCAGATATAGGATAGCATATACTACCCAGATATAGATTAGGATAGCATATG
CTACCCAGATATAGGATAGCATATGCTATCCAGATATTTGGGTAGTATATGCTACCCAGATTAGGATAG
ATAGATTAGGATAGCATATGCTATCCAGATATTGCTACCCGGATACAGATTAGGATAGCATATACTAC
CATATACTACCCTAATCTCTATTAGGATAGCATATGCTACCCGGATAGCCTATGCTACCCAGATATAA
CCAGATATAGATTAGGATAGCATATACTACCCAGATATAGGATAGCATATGCTACCCAGATATAGGATAG
ATTAGGATAGCATATACTACCCAGATATAGGATAGCATATGCTACCCAGATATAGATTAGGATAG
CCTATGCTACCCAGATATAGGATAGCATATGCTATCCAGATATTGGGTAGTATATGCTACCCAT
GGCAACATTAGCCCACCGTGCTCTCAGCGACCTCGTGAATATGAGGACCAACCCTGTCTTGGCGCT
CAGGCGCAAGTGTGTAATTTGTCTCCAGATCGCAGCAATCGCGCCCTATCTTGGCCCGCCACCTA
CTTATGCAGGTATTCCCCGGGTGGTCCCATTAGTGGTTTTGTGGGCAAGTGGTTTGACCCGCCAGTGGTTAGCG
GGGTTACAATCAGCCAAGTTATTACACCCTTATTTTACAGTCCAAAACCGCAGGCGCGGCGTGTGGGGCT
GACGCGTGCCCCACTCCACAATTCAAAAAAAGAGTGGCCACTTGTCTTTGTTATGGCCCATTGG
CGTGGAGCCCCGTTTAATTTCGGGGGTGTTAGAGACAACCAGTGGAGTCCGCTGTCTTCGGCGTCCACT
CTCTTCCCCTTGTTACAAATAGAGTGTAACAACATGTTCACCTGTCTTGCCCATAGCCATAAATTCGTGTGAGATGG
CTTAATAACCCAGTATCATATTGCACTAGGATTATGTGCCCATGGATTTCTATTGTTAAAGATATTCAGAATGTTCATT
ACATCCAGTCTTTACGGCTTGTCCCCACCCCATGGGTTTGTGAGGGTTATATTGGTGTCATAGCACAATGCCACCACT
CCTACACTAGTATTATTGCCCAAGGGTTTGGGGGCGTCACCTGAAACCTTGTTTTCGAGCACCTCACATACACC
GAACCCCCGTCAAATTTTATTCTGGGGGCGTCACCTGAAACCTTGTTTTCGAGCACCTCACATACACC
TTACTGTTCACAACTGCTGCCCGCTCCCTTGATCTTCAGCCACTGCCCTTGTGACTAAAATGGTTCACTACCCTCGT
GGAGAGTTCACTGCCCGCCATGTAAAATAAAACCGTGACAGCTCATGGGGTGGGAGATATGCTGTTCCTTAGGAC
GGAATCCCTGACCCCATGTAAAATAAAACCGTGACAGCTCATGGGGTGGGAGATATGCTGTTCCTTAGGAC
CCTTTTACTAACCCTAATTCGATAGCATATGCTTCCCGTTGGGTAACATATGCTATTGAATTAGGTTAG
TCTGGATAGTATATACTACCCGGAAGCATATGCTACCCGTTTAGGTTAACAAGGGGCCTATAA
ACACTATTGCTAATGCCCCTCTTGAGGTCCGCTTATCGGTAGCTACACAGCCCCCTCTGATTGACGTTGG
TGTAGCCTCCCGTAGTCTTCCTGGGCCCCTGGGAGGTACATGTCCC
```

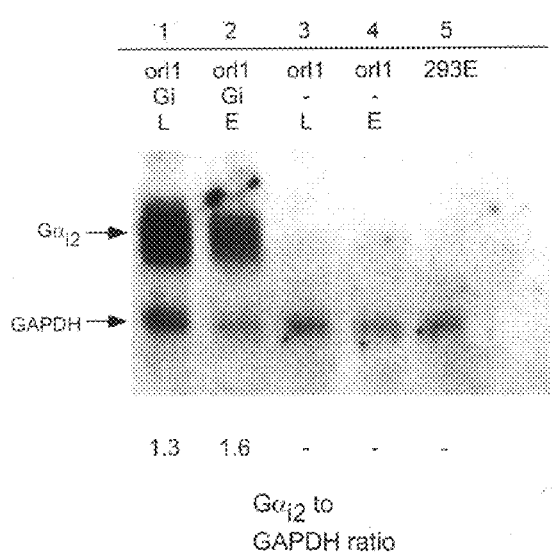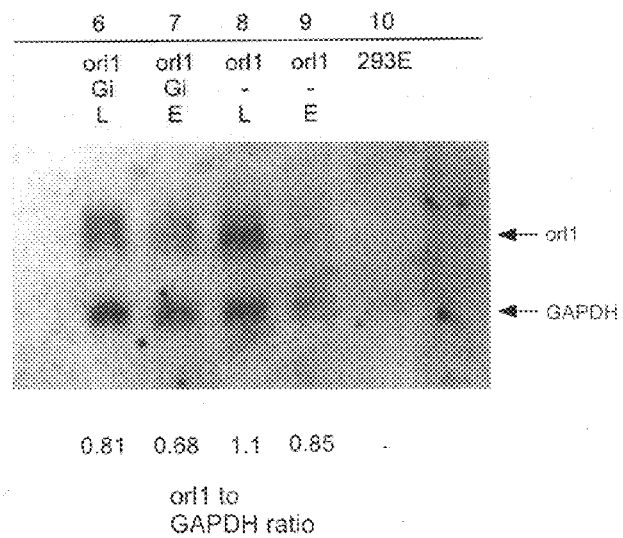
FIG. 16A
FIG. 16B

SEQUENCE LISTING

<160> NUMBER OF SEQ ID NOS: 36

<210> SEQ ID NO 1
<211> LENGTH: 5452
<212> TYPE: DNA
<213> ORGANISM: VEBNA

<400> SEQUENCE: 1

| | | | | | |
|---|---|---|---|---|---|
| tcgcgcgttt | cggtgatgac | ggtgaaaacc | tctgacacat | gcagctcccg | gagacggtca | 60 |
| cagcttgtct | gtaagcggat | gccgggagca | gacaagcccg | tcagggcgcg | tcagcgggtg | 120 |
| ttggcgggtg | tcggggctgg | cttaactatg | cggcatcaga | gcagattgta | ctgagagtgc | 180 |
| accatatgcg | gtgtgaaata | ccgcacagat | gcgtaaggag | aaaataccgc | atcaggcgcc | 240 |
| attcgccatt | caggctgcgc | aactgttggg | aagggcgatc | ggtgcgggcc | tcttcgctat | 300 |
| tacgccagct | ggcgaaaggg | ggatgtgctg | caaggcgatt | aagttgggta | acgccagggt | 360 |
| tttcccagtc | acgacgttgt | aaaacgacgg | ccagtgccaa | gcttgcatgc | ctgcaggtct | 420 |
| actgggatt | tattctttag | tgcggggaa | tacacggctt | ttaatacgat | tgagggcgtc | 480 |
| tcctaacaag | ttacatcact | cctgcccttc | ctcaccctca | tctccatcac | ctccttcatc | 540 |
| tccgtcatct | ccgtcatcac | cctccgcggc | agccccttcc | accataggtg | gaaaccaggg | 600 |
| aggcaaatct | actccatcgt | caaagctgca | cacagtcacc | ctgatattgc | aggtaggagc | 660 |
| gggctttgtc | ataacaaggt | ccttaatcgc | atccttcaaa | acctcagcaa | atatatgagt | 720 |
| ttgtaaaaag | accatgaaat | aacagacaat | ggactccctt | agcgggccag | ttgtgggcc | 780 |
| gggtccaggg | gccattccaa | aggggagacg | actcaatggt | gtaagacgac | attgtggaat | 840 |
| agcaagggca | gttcctcgcc | ttaggttgta | aagggaggtc | ttactacctc | catatacgaa | 900 |
| cacaccggcg | acccaagttc | cttcgtcggt | agtcctttct | acgtgactcc | tagccaggag | 960 |
| agctcttaaa | ccttctgcaa | tgttctcaaa | tttcgggttg | gaacctcctt | gaccacgatg | 1020 |
| cttttccaaac | caccctcctt | ttttgcgcct | gcctccatca | ccctgacccc | ggggtccagt | 1080 |
| gcttgggcct | tctcctgggt | catctgcggg | gccctgctct | atcgctcccg | ggggcacgtc | 1140 |
| aggctcacca | tctgggccac | cttcttggtg | gtattcaaaa | taatcggctt | ccctacagg | 1200 |
| gtggaaaaat | ggccttctac | ctggaggggg | cctgcgcggt | ggagacccgg | atgatgatga | 1260 |
| ctgactactg | ggactcctgg | gcctcttttc | tccacgtcca | cgacctctcc | ccctggctct | 1320 |
| ttcacgactt | ccccccctgg | ctctttcacg | tcctctaccc | cggcggcctc | cactacctcc | 1380 |
| tcgaccccgg | cctccactac | ctcctcgacc | ccggcctcca | ctgcctcctc | gaccccggcc | 1440 |
| tccacctcct | gctcctgccc | ctcctgctcc | tgccctcct | cctgctcctg | cccctcctgc | 1500 |
| ccctcctgct | cctgcccctc | ctgccctcc | tgctcctgcc | cctcctgccc | ctcctgctcc | 1560 |
| tgcccctcct | gccctcctc | ctgctcctgc | cctcctgcc | cctcctgctg | ctcctgcccc | 1620 |
| tcctgcccct | cctgctcctg | cccctcctgc | cctcctgct | ctgcccctc | ctgcccctcc | 1680 |
| tgctcctgcc | cctcctgctc | ctgcccctcc | tgctcctgcc | cctcctgctc | ctgcccctcc | 1740 |
| tgcccctcct | gccctcctc | ctgctcctgc | cctcctgct | ctgcccctc | ctgcccctcc | 1800 |
| tgcccctcct | gctcctgccc | ctcctcctgc | tcctgcccct | cctgcccctc | ctgcccctcc | 1860 |
| tcctgctcct | gcccctcctg | cccctcctc | tgctcctgcc | cctcctcctg | ctcctgcccc | 1920 |
| tcctgcccct | ctgcccctc | ctcctgctcc | tgcccctcct | gcccctcctc | ctgctcctgc | 1980 |
| ccctcctcct | gctcctgccc | ctcctgcccc | tcctgcccct | cctcctgctc | ctgcccctcc | 2040 |

```
tcctgctcct gccctcctg ccctcctgc cctcctgcc cctcctcctg ctcctgcccc    2100
tcctcctgct cctgccctc ctgctcctgc ccctcccgct cctgctcctg ctcctgttcc    2160
accgtgggtc cctttgcagc caatgcaact tggacgtttt tggggtctcc ggacaccatc    2220
tctatgtctt ggccctgatc ctgagccgcc cggggctcct ggtcttccgc ctcctcgtcc    2280
tcgtcctctt ccccgtcctc gtccatggtt atcaccccct cttctttgag gtccactgcc    2340
gccggagcct tctggtccag atgtgtctcc cttctctcct aggccatttc caggtcctgt    2400
acctggcccc tcgtcagaca tgattcacac taaaagagat cccgggtac ccggggatcc    2460 tctagagtca ggctggatcg gtcccggtgt cttctatgga ggtcaaaaca gcgtggatgg    2520
cgtctccagg cgatctgacg gttcactaaa cgagctctgc ttatatagac ctcccaccgt    2580
acacgcctac cgcccatttg cgtcaatggg gcggagttgt tacgacattt tggaaagtcc    2640
cgttgatttt ggtgccaaaa caaactccca ttgacgtcaa tggggtggag acttggaaat    2700
ccccgtgagt caaaccgcta tccacgccca ttgatgtact gccaaaaccg catcaccatg    2760
gtaatagcga tgactaatac gtagatgtac tgccaagtag gaaagtccca taaggtcatg    2820
tactgggcat aatgccaggc gggccattta ccgtcattga cgtcaatagg gggcgtactt    2880
ggcatatgat acacttgatg tactgccaag tgggcagttt accgtaaata ctccacccat    2940
tgacgtcaat ggaaagtccc tattggcgtt actatgggaa catacgtcat tattgacgtc    3000
aatgggcggg ggtcgttggg cggtcagcca ggcgggccat ttaccgtaag ttatgtaacg    3060
cggaactcca tatatgggct atgaactaat gaccccgtaa ttgattacta ttaataacta    3120
gtcaataatc aatgtcaaca tggcggtaat gttggacatg agccaatata aatgtacata    3180
ttatgatatg gatacaacgt atgcaatggg ccaagcttgg cgtaatcatg gtcatagctg    3240
tttcctgtgt gaaattgtta tccgctcaca attccacaca acatacgagc cggaagcata    3300
aagtgtaaag cctggggtgc ctaatgagtg agctaactca cattaattgc gttgcgctca    3360
ctgcccgctt tccagtcggg aaacctgtcg tgccagctgc attaatgaat cggccaacgc    3420
gcggggagag gcggtttgcg tattgggcgc tcttccgctt cctcgctcac tgactcgctg    3480
cgctcggtcg ttcggctgcg gcgagcggta tcagctcact caaaggcggt aatacggtta    3540
tccacagaat caggggataa cgcaggaaag aacatgtgag caaaaggcca gcaaaaggcc    3600
aggaaccgta aaaaggccgc gttgctggcg ttttttccata ggctccgccc cctgacgag    3660 catcacaaaa atcgacgctc aagtcagagg tggcgaaacc cgacaggact ataaagatac    3720
caggcgtttc ccctggaag ctccctcgtg cgctctcctg ttccgaccct gccgcttacc    3780
ggatacctgt ccgcctttct cccttcggga agcgtggcgc tttctcatag ctcacgctgt    3840
aggtatctca gttcggtgta ggtcgttcgc tccaagctgg gctgtgtgca cgaaccccc    3900 gttcagcccg accgctgcgc cttatccggt aactatcgtc ttgagtccaa cccggtaaga    3960
cacgacttat cgccactggc agcagccact ggtaacagga ttagcagagc gaggtatgta    4020
ggcggtgcta cagagttctt gaagtggtgg cctaactacg gctacactag aaggacagta    4080
tttggtatct gcgctctgct gaagccagtt accttcggaa aaagagttgg tagctcttga    4140
tccggcaaac aaaccaccgc tggtagcggt ggtttttttg tttgcaagca gcagattacg    4200
cgcagaaaaa aaggatctca agaagatcct ttgatctttt ctacgggtc tgacgctcag    4260 tggaacgaaa actcacgtta agggattttg gtcatgagat tatcaaaaag gatcttcacc    4320
tagatccttt taaattaaaa atgaagtttt aaatcaatct aaagtatata tgagtaaact    4380
tggtctgaca gttaccaatg cttaatcagt gaggcaccta tctcagcgat ctgtctattt    4440
```

-continued

```
cgttcatcca tagttgcctg actccccgtc gtgtagataa ctacgatacg ggagggctta    4500
ccatctggcc ccagtgctgc aatgataccg cgagacccac gctcaccggc tccagattta    4560
tcagcaataa accagccagc cggaagggcc gagcgcagaa gtggtcctgc aactttatcc    4620
gcctccatcc agtctattaa ttgttgccgg gaagctagag taagtagttc gccagttaat    4680
agtttgcgca acgttgttgc cattgctaca ggcatcgtgg tgtcacgctc gtcgtttggt    4740
atggcttcat tcagctccgg ttcccaacga tcaaggcgag ttacatgatc ccccatgttg    4800
tgcaaaaaag cggttagctc cttcggtcct ccgatcgttg tcagaagtaa gttggccgca    4860
gtgttatcac tcatggttat ggcagcactg cataattctc ttactgtcat gccatccgta    4920
agatgctttt ctgtgactgg tgagtactca accaagtcat tctgagaata gtgtatgcgg    4980
cgaccgagtt gctcttgccc ggcgtcaata cgggataata ccgcgccaca tagcagaact    5040
ttaaaagtgc tcatcattgg aaaacgttct cggggcgaaa actctcaag gatcttaccg    5100 ctgttgagat ccagttcgat gtaacccact cgtgcaccca actgatcttc agcatctttt    5160
actttcacca gcgtttctgg gtgagcaaaa acaggaaggc aaaatgccgc aaaaaaggga    5220
ataagggcga cacggaaatg ttgaatactc atactcttcc ttttcaata ttattgaagc    5280 atttatcagg gttattgtct catgagcgga tacatatttg aatgtattta gaaaaataaa    5340 caaataggg ttccgcgcac atttccccga aaagtgccac ctgacgtcta agaaaccatt    5400
attatcatga cattaaccta taaaaatagg cgtatcacga ggccctttcg tc            5452
```

<210> SEQ ID NO 2
<211> LENGTH: 1931
<212> TYPE: DNA
<213> ORGANISM: EBNA

<400> SEQUENCE: 2

```
tacagactgc tccccggtcc atgtcctgga cctttaccgg atcctctctt ccctctgtgt      60
agacctggtc ttccgaggcc gccgtcacct ggagtttctt ctcccccact attggtacct     120
gctcctgccc cttctcctgc tcctgctcct ccgccttctg gtcctcgggg cccgccgagt     180
cctagtcccg gttctgtatc tctaccacag gcctctgggg ttttttgcagg ttcaacgtaa    240 ccgacgtttc cctgggtgcc accttgtcct cgtcctcgtc ctcgccctcc ccgtcctcgt     300
cctccccgtc ctcgtcctcc tccccgtcct cgtcctcctc ccgtcctcc ccgtcctccc      360 cgtcctcccc gtcctcgtcc tcctcccgt cctcgtcctc ctcccgtcc tcccgtcct       420 ccccgtcctc gtcctcctcc ccgtcctcgt cctcctcccc gtcctccccg tcctcgtcct     480 cctcccgtc ctcccgtcc tcccgtcct cgtcctcctc ccgtcctcg tcctcctccc        540 cgtcctcccc gtcctcgtcc tcctcccgt cctcccgtc tcgtcctcct ccgtcctcct       600
ccccgtcctc gtcctcccg tcctcccgt cctcccgtc ctcgtcctcc ccgtcctcgt        660
cctcctcccc gtcctcccg tcctcccgt cctcgtcctc ccgtcctcg tcctcccgt         720 cctcgtcctc ccgtcctcg tcctcccgt cctcccgtc ctcgtcctcc ccgtcctccc        780
cgtcctcgtc tcccgtcc tcccgtcct cgtcctcctc ccgtcctcc ccgtcctcgt         840 cctcctcccc gtcctcccg tcctcgtcct cccgtcctc ccgtcctcg tcctcccgt         900 cctcccgtc tcgtcctcc ccgtcctccc cgtcctcgtc tcctcccg tcctcgtcct         960 ccccgtcctc gtcctccacc tccggcccca gctcctccgt cacctccggc cccagctcct    1020
ccatcacctc cggcccagc tcctccatca cctcggcgg cccatctcc tgcactttct       1080 cggtccccc cttcagcact ttctcggtcc ccctctccag cacctgcacc tcttttctcc    1140
```

```
gggtcctcag ggtcatcagt cagtagtagt aggcccagag gtggcgcgtc cgggggaggt    1200
ccatcttccg gtaaaaaggt gggacatccc cttcggctaa taaaacttat ggtggttctt    1260
ccaccgggtc taccactcgg actgcacggg ggccctcgct atctcgtccc ggggcgtcta    1320
ctgggtcctc ttccgggttc gtgacctggg gccccagtcc cactacctcc gtccgcgttt    1380
tttcctccca ccaaacccttt cgtagcacca gttcctccaa ggttgggctt taaactcttg    1440
taacgtcttc caaattctcg agaggaccga tcctcagtgc atctttcctg atggctgctt    1500
ccttgaaccc agcggccaca caagcatata cctccatcat tctggaggga aatgttggat    1560
tccgctcctt gacgggaacg ataaggtgtt acagcagaat gtggtaactc agcagagggg    1620
aaaccttacc ggggacctgg gccggtgtt ggaccgggcg attccctcag gtaacagaca    1680
ataaagtacc agaaaaatgt ttgagtatat aaacgactcc aaaacttcct acgctaattc    1740
ctggaacaat actgtttcgg gcgaggatgg acgttatagt cccactgaca cacgtcgaaa    1800
ctgctacctc atctaaacgg agggaccaaa ggtggatacc accttccccg acggcgcctc    1860
ccactactgc ctctactgcc tctacttcct ccactacctc tactcccact ccttcccgtc    1920
ctcactacat t                                                         1931
```

<210> SEQ ID NO 3
<211> LENGTH: 1801
<212> TYPE: DNA
<213> ORGANISM: Epstein Barr Virus

<400> SEQUENCE: 3

```
gcaggaaaag gacaagcagc gaaaattcac gccccttgg gaggtggcgg catatgcaaa      60
ggatagcact cccactctac tactgggtat catatgctga ctgtatatgc atgaggatag     120
catatgctac ccggatacag attaggatag catatactac ccagatatag attaggatag     180
catatgctac ccagatatag attaggatag cctatgctac ccagatataa attaggatag     240
catatactac ccagatatag attaggatag catatgctac ccagatatag attaggatag     300
cctatgctac ccagatatag attaggatag catatgctac ccagatatag attaggatag     360
catatgctat ccagatattt gggtagtata tgctacccag atataaatta ggatagcata     420
tactacccta atctctatta ggatagcata tgctacccgg atacagatta ggatagcata     480
tactacccag atatagatta ggatagcata tgctacccag atatagatta ggatagccta     540
tgctacccag atataaatta ggatagcata tactacccag atatagatta ggatagcata     600
tgctacccag atatagatta ggatagccta tgctacccag atatagatta ggatagcata     660
tgctatccag atatttgggt agtatatgct acccatggca acattagccc accgtgctct     720
cagcgacctc gtgaatatga ggaccaacaa ccctgtgctt ggcgctcagg cgcaagtgtg     780
tgtaatttgt cctccagatc gcagcaatcg cgccctatc ttggcccgcc cacctactta     840
tgcaggtatt cccgggggtg ccattagtgg ttttgtgggc aagtggtttg accgcagtgg     900
ttagcggggt tacaatcagc caagttatta caccttatt ttacagtcca aaaccgcagg     960
gcggcgtgtg ggggctgacg cgtgccccca ctccacaatt tcaaaaaaaa gagtggccac    1020
ttgtctttgt ttatgggccc cattggcgtg gagcccgtt taattttcgg gggtgttaga    1080
gacaaccagt ggagtccgct gctgtcggcg tccactctct ttccccttgt tacaaataga    1140
gtgtaacaac atggttcacc tgtcttggtc cctgcctggg acacatctta ataaccccag    1200
tatcatattg cactaggatt atgtgttgcc catagccata aattcgtgtg agatggacat    1260 ccagtctttta cggcttgtcc ccaccccatg gatttctatt gttaaagata ttcagaatgt    1320
ttcattccta cactagtatt tattgcccaa gggggtttgtg agggttatat tggtgtcata    1380
```

```
gcacaatgcc accactgaac cccccgtcca aattttattc tggggcgtc acctgaaacc      1440 ttgttttcga gcacctcaca tacaccttac tgttcacaac tcagcagtta ttctattagc     1500
taaacgaagg agaatgaaga agcaggcgaa gattcaggag agttcactgc ccgctccttg     1560
atcttcagcc actgcccttg tgactaaaat ggttcactac cctcgtggaa tcctgacccc    1620
atgtaaataa aaccgtgaca gctcatgggg tgggagatat cgctgttcct taggaccctt    1680
ttactaaccc taattcgata gcatatgctt cccgttgggt aacatatgct attgaattag    1740
ggttagtctg gatagtatat actactaccc gggaagcata tgctacccgt ttagggttaa    1800
c                                                                    1801
```

<210> SEQ ID NO 4
<211> LENGTH: 26
<212> TYPE: DNA
<213> ORGANISM: pBSIISK(+)

<400> SEQUENCE: 4

```
atatcataat atgtacattt atattg                                         26
```

<210> SEQ ID NO 5
<211> LENGTH: 41
<212> TYPE: DNA
<213> ORGANISM: pBSIISK(+)

<400> SEQUENCE: 5

```
tcgcgacgtc tccgtgtagg cgatctgacg gttcactaaa c                        41
```

<210> SEQ ID NO 6
<211> LENGTH: 57
<212> TYPE: DNA
<213> ORGANISM: Vector p394

<400> SEQUENCE: 6

```
aattcgcgac gcgtgatatc tgcaggccta gatctctaga taagtaatga tcatgca       57
```

<210> SEQ ID NO 7
<211> LENGTH: 49
<212> TYPE: DNA
<213> ORGANISM: Vector p394

<400> SEQUENCE: 7

```
tgatcattac ttatctagag atctaggcct gcagatatca cgcgtcgcg                49
```

<210> SEQ ID NO 8
<211> LENGTH: 27
<212> TYPE: DNA
<213> ORGANISM: CCR3 Vector

<400> SEQUENCE: 8

```
gtgaaatgac aacctcacta gatacag                                        27
```

<210> SEQ ID NO 9
<211> LENGTH: 24
<212> TYPE: DNA
<213> ORGANISM: CCR3

<400> SEQUENCE: 9

```
ctgacctaaa acacaataga gagt                                           24
```

<210> SEQ ID NO 10
<211> LENGTH: 23
<212> TYPE: DNA

```
<213> ORGANISM: CCR3

<400> SEQUENCE: 10
tgtcgattgt cagcaggatt atg                                    23

<210> SEQ ID NO 11
<211> LENGTH: 57
<212> TYPE: DNA
<213> ORGANISM: CCR3

<400> SEQUENCE: 11
gttctgtctc tgctgccact gctcgaggct caaacaacct cactagatac agttgag    57

<210> SEQ ID NO 12
<211> LENGTH: 62
<212> TYPE: DNA
<213> ORGANISM: CCR3

<400> SEQUENCE: 12
gagcagccgg caccaccatg gctctgtctt gggttctgac tgttctgtct ctgctgccac  60
tg                                                                62

<210> SEQ ID NO 13
<211> LENGTH: 23
<212> TYPE: DNA
<213> ORGANISM: pE3 Vector

<400> SEQUENCE: 13
cgatcacgtg cagctgagat cta                                    23

<210> SEQ ID NO 14
<211> LENGTH: 25
<212> TYPE: DNA
<213> ORGANISM: pE3delta

<400> SEQUENCE: 14
catgtagatc tcagctgcac gtgat                                  25

<210> SEQ ID NO 15
<211> LENGTH: 35
<212> TYPE: DNA
<213> ORGANISM: pm3or11

<400> SEQUENCE: 15
ccctctagac catggagccc ctcttccccg cgccg                       35

<210> SEQ ID NO 16
<211> LENGTH: 35
<212> TYPE: DNA
<213> ORGANISM: pm3or11

<400> SEQUENCE: 16
ccctctagac caggcaccat gggcaggtcc acgcc                       35

<210> SEQ ID NO 17
<211> LENGTH: 44
<212> TYPE: DNA
<213> ORGANISM: pE3zeocretkluc

<400> SEQUENCE: 17
ctccggatcc tccttggctg acgtcagtag agagatccca tggc             44

<210> SEQ ID NO 18
```

```
<211> LENGTH: 40
<212> TYPE: DNA
<213> ORGANISM: pE3zeocretkluc

<400> SEQUENCE: 18
atctctctac tgacgtcagc caaggaggat ccggagagct                    40

<210> SEQ ID NO 19
<211> LENGTH: 47
<212> TYPE: DNA
<213> ORGANISM: pE3zeocretkluc

<400> SEQUENCE: 19
cgtcatactg tgacgtcttt cagacacccc attgacgtca atgggag             47

<210> SEQ ID NO 20
<211> LENGTH: 49
<212> TYPE: DNA
<213> ORGANISM: pE3zeocretkluc

<400> SEQUENCE: 20
ttgacgtcaa tggggtgtct gaaagacgtc acagtatgac ggccatggg          49

<210> SEQ ID NO 21
<211> LENGTH: 43
<212> TYPE: DNA
<213> ORGANISM: pE3zeocretkluc

<400> SEQUENCE: 21
ggtaccgcac cagacagtga cgtcagctgc cagatcccat ggc                43

<210> SEQ ID NO 22
<211> LENGTH: 42
<212> TYPE: DNA
<213> ORGANISM: pE3zeocretkluc

<400> SEQUENCE: 22
gatctggcag ctgacgtcac tgtctggtgc ggtaccctcc ca                 42

<210> SEQ ID NO 23
<211> LENGTH: 48
<212> TYPE: DNA
<213> ORGANISM: pE3zeocretkluc

<400> SEQUENCE: 23
cgtcatactg tgacgtcttt cagacacccc attgacgtca atgggaga           48

<210> SEQ ID NO 24
<211> LENGTH: 59
<212> TYPE: DNA
<213> ORGANISM: pE3zeocretkluc

<400> SEQUENCE: 24
gatctctccc attgacgtca atgggtgtc tgaaagacgt cacagtatga cggccatgg  59

<210> SEQ ID NO 25
<211> LENGTH: 40
<212> TYPE: DNA
<213> ORGANISM: pE3zeocretkluc

<400> SEQUENCE: 25
ttttagatct cagaagccga attcgaacac gcagatgcag                    40

<210> SEQ ID NO 26
```

```
<211> LENGTH: 31
<212> TYPE: DNA
<213> ORGANISM: pE3zeocretkluc

<400> SEQUENCE: 26
aaaactcgag attgcggcac gctgttgacg c                              31

<210> SEQ ID NO 27
<211> LENGTH: 35
<212> TYPE: DNA
<213> ORGANISM: pHEBomcs5

<400> SEQUENCE: 27
ctcgagaagc ttggccggcc agatctgcgg ccgcg                          35

<210> SEQ ID NO 28
<211> LENGTH: 23
<212> TYPE: DNA
<213> ORGANISM: pE3zeocretkluc

<400> SEQUENCE: 28
cgatcacgtg cagctgagat cta                                       23

<210> SEQ ID NO 29
<211> LENGTH: 25
<212> TYPE: DNA
<213> ORGANISM: pE3zeocretkluc

<400> SEQUENCE: 29
catgtagatc tcagctgcac gtgat                                     25

<210> SEQ ID NO 30
<211> LENGTH: 27
<212> TYPE: DNA
<213> ORGANISM: pm3CCR2

<400> SEQUENCE: 30
ccacaacatg ctgtccacat ctcgttc                                   27

<210> SEQ ID NO 31
<211> LENGTH: 21
<212> TYPE: DNA
<213> ORGANISM: pm3CCR2

<400> SEQUENCE: 31
cctctagaga ccagccgaga c                                         21

<210> SEQ ID NO 32
<211> LENGTH: 59
<212> TYPE: DNA
<213> ORGANISM: pm3CCR2sp

<400> SEQUENCE: 32
taaccggtca ccatggcttc cctggctcgt gcgatgctgg ctctgctggc tctgtacgc  59

<210> SEQ ID NO 33
<211> LENGTH: 66
<212> TYPE: DNA
<213> ORGANISM: pm3CCR2sp

<400> SEQUENCE: 33
ctggctctgc tggctctgta cgctgctgct atcgctgctg ctccactgtc cacatctcgt  60
tctcgg                                                          66
```

```
<210> SEQ ID NO 34
<211> LENGTH: 20
<212> TYPE: DNA
<213> ORGANISM: pm3CCR2sp

<400> SEQUENCE: 34
ccagcgagta gagcggaggc                                                    20

<210> SEQ ID NO 35
<211> LENGTH: 35
<212> TYPE: DNA
<213> ORGANISM: pm3or11

<400> SEQUENCE: 35
ccctctagac catggagccc ctcttccccg cgccg                                   35

<210> SEQ ID NO 36
<211> LENGTH: 35
<212> TYPE: DNA
<213> ORGANISM: pm3or11

<400> SEQUENCE: 36
ccctctagac caggcaccat gggcaggtcc acgcc                                   35
```

EUKARYOTIC CELLS STABLY EXPRESSING GENES FROM MULTIPLE TRANSFECTED EPISOMES

This application is a continuation-in-part of Ser. No. 09/040,961, filed Mar. 18, 1998.

BACKGROUND OF THE INVENTION

In the field of molecular biology it is often desirable to transfect cells to express multiple genes. Classical methods for achieving this have relied upon integration of multiple genes into one or more chromosomal loci. The sites of gene integration, however, are random, and the number and ratio of genes integrating at any particular site are unpredictable. Therefore every transfected cell is unique. Furthermore, expression of the integrated genes may be subject to unpredictable position effects, e.g., those caused by adjacent chromosomal sequences. In some cases, amplification of the genes of interest is required in order to achieve adequate expression levels. As a result, it is normally necessary to screen many clonal cell populations to obtain a cell line in which all of the desired genes are expressed at an appropriate level. This procedure of transfection, selection and analysis of numerous clonally derived cell lines expressing the multiple genes can take many months.

For example, simultaneous transfection of HEK293 cells with vectors encoding the $\alpha1$, $\alpha2$, and $\beta3$ subunits of human calcium channel has been carried out to obtain fully functional expression of that multi-subunit protein from chromosomally incorporated copies of the transfected genes. However, obtaining cells that functionally express all three subunits requires extensive screening of cell populations, while finally obtaining very few colonies (Buchert et al., *Biotechniques* (UNITED STATES) 23, 402–407, 1997).

Non-integrating, autonomously replicating episomal vectors have been used to transform cells to express a gene of interest. In particular, the Epstein Barr Virus (EBV) Nuclear Antigen 1 (EBNA 1) has been used to stably maintain a plasmid containing an EBV origin of replication (oriP) in primate cells (Reisman, D. et al, *Mol. Cell. Biol.* 5: 1822–1832, 1985; Yates, J. L. et al., *Nature* 313:812–815, 1985). The plasmid is maintained in an episomal state, i.e., it is not integrated into the chromosome.

Transfection of cell lines that express EBNA 1 can be advantageous since the ability of such cells to stably maintain an episomal construct can be enhanced by several orders of magnitude, and stable cell lines can be generated in as little as two to three weeks. For example, HEK cells that stably express EBNA 1 have been transformed with plasmids containing the EBV origin of replication, and the gene encoding CRHR1 (corticotropin releasing hormone receptor subtype I). The resulting cell lines have been found to stably express high levels of CRHR1. (Horlick et al., *Prot. Exp. And. Purific.* 9:301–308, 1997.)

Similarly, U.S. Pat. No. 4,686,186 describes transfecting cells with a single plasmid containing the EBV oriP, the EBNA 1 gene, and a gene encoding a protein of interest (U.S. Pat. No. 4,686,186).

Expression of multiple genes on a single plasmid, however, can result in promoter occlusion. (Greger, I. H. et al., *Nuc. Acid Res.* 26(5): 1214–1301, 1998; Kadesch, T. et al., *Mol. Cell. Biol.* 6(7): 2593–2601, 1986). In cases of promoter occlusion, one strong promoter can bind most or all of the transcription factors in its immediate vicinity, thereby limiting transcription from other promoters present in cis on the same plasmid. This, in turn, causes the expression of multiple genes of interest on a single episome to be unpredictable and often problematic (Horlick et al., 1997). The EBNA1/oriP expression system has not, therefore been widely used to express multiple genes of interest.

Currently, each cell type for which episomal expression is desired is typically first transfected with an integrating copy of the gene encoding EBNA 1. Since developing cell lines that constitutively express EBNA 1 from an integrated gene is time consuming, current methods are somewhat limited in their applicability to different cell lines. Programs for mass screening of compound libraries require use of many types of cell lines, and producing EBNA 1 producing strains of each type by this method requires an extensive effort.

Alternately, episomes that already carry the EBNA 1 gene and a gene of interest in cis on the same episome can be used to transfect cells. Commercial vectors such as pCEP4 (Invitrogen) are available for this purpose. However, current vectors in which EBNA 1 is carried by the episomal construct in cis do not contain a known promoter for driving expression of EBNA 1. Rather, it is believed that transcription of the EBNA 1 gene occurs from a fortuitous promoter situated in or near an amp resistance marker that is located a few hundred nucleotides upstream from the EBNA 1 start codon. This fortuitous promoter, however, is not sufficiently recognized by differing cell types to consistently express EBNA-1 with sufficient speed and abundance to sustain the replication and maintenance of the episome (before it is otherwise lost from the cell). Therefore, currently available episomal vectors containing the EBNA 1 gene in cis do not appear to provide sufficient reliability for use in a wide variety of cell types. Furthermore, adding a strong promoter to these episomes to express the EBNA-1 gene in cis would, under certain circumstances, result in promoter occlusion.

Multiple plasmids have been used to transform bacterial cells. However, to the inventors's knowledge, transfection of eukaryotic cells with multiple plasmids has not been described. Furthermore, it has not been known whether transfecting a eukaryotic cell with a second or third episome would disrupt an already resident first episome. For example, it has not been known whether transfection of separate episomal constructs into eukaryotic cells would result in stable maintenance of both constructs, or in efficient transcription or translation of separate genes contained in both constructs.

There is therefore a need for a method that allows rapid production of eukaryotic cells that stably express multiple genes.

There is also a need for a method that allows rapid production of stable cell lines of varying types that express a gene of interest.

SUMMARY OF THE INVENTION

The present invention provides a method for producing recombinant eukaryotic cell lines expressing multiple proteins of interest, by transfecting eukaryotic host cells with (a) a first episome which contains an EBV origin of replication and a first gene encoding a protein of interest; and (b) a second episome containing an EBV origin of replication and a second gene encoding a protein of interest. Transfected cells are obtained, those cells expressing an EBNA 1 protein. The cells are grown under conditions wherein the episomes express the first and second genes.

In another aspect, the invention relates to a method involving the steps of:

(i) transfecting a host cell line with (a) a first episome which comprises an EBV origin of replication, and a gene encoding an EBNA 1 protein; and (b) a second episome comprising the EBV origin of replication, a gene encoding a protein to be expressed by the cell line, and a selectable marker for eukaryotic cells, to produce transfected cells; and (ii) growing the transfected cells in medium wherein cells which express the selectable marker and the EBNA 1 protein survive, for a time sufficient to allow cell propagation. Preferably, expression of both the EBNA 1 protein and the gene of interest on the second episome is driven by strong promoters.

In another aspect, the present invention provides a recombinant eukaryotic cell transfected with first and second episomes. The first episome contains an EBV origin of replication and a gene encoding a first protein. The second episome contains an EBV origin of replication, and a gene encoding a second protein. The recombinant eukaryotic cell expresses an EBNA 1 protein from a previously transfected integrated copy of the EBNA 1 gene.

These and other aspects of the present invention will be apparent to those of ordinary skill in the art in light of the present specification, claims and drawings.

BRIEF DESCRIPTION OF THE DRAWINGS

FIG. 1 shows the nucleotide sequence of plasmid pCM-VEBNA (SEQ ID NO:1).

FIG. 2 shows the nucleotide sequence of full-length EBNA 1 in the correct orientation (SEQ ID NO:2).

FIG. 3 shows the nucleotide sequence of EBV oriP (SEQ ID NO:3).

FIG. 16 is a Northern blot analyses of RNA isolated from early and late passage 293no, and 293 noiHP cells probed with Giα2 or ORL1.

DETAILED DESCRIPTION OF THE INVENTION

Figure 4:
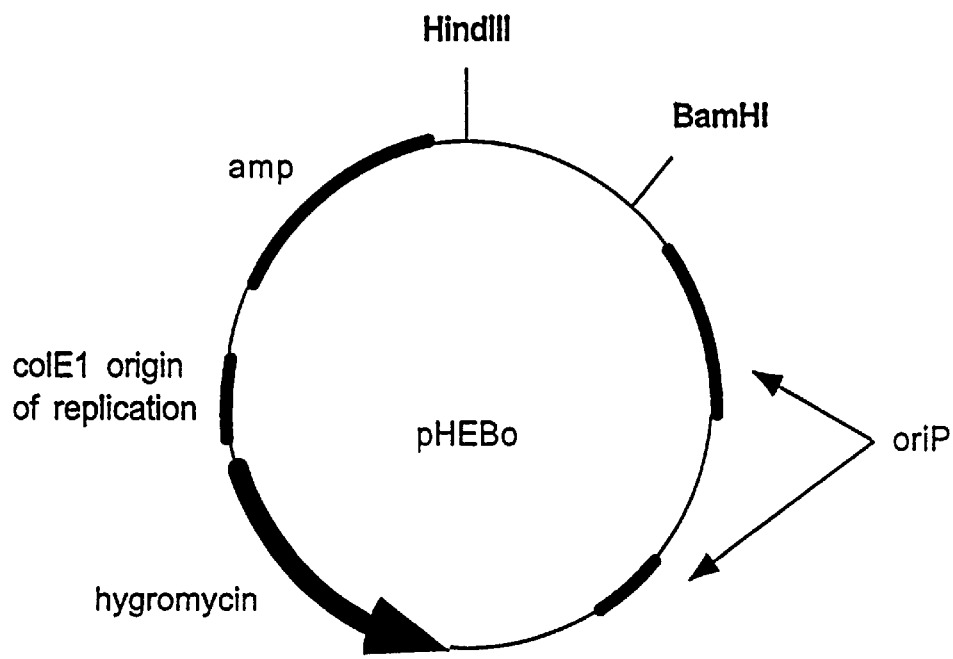
FIG. 4 shows vector pHEBo schematically.

All patent applications, patents and literature references cited herein are hereby incorporated by reference in their entirety.

In practicing the present invention, many conventional techniques in molecular biology, microbiology, and recombinant DNA are used. These techniques are well known and are explained in, for example, *Current Protocols in Molecular Biology*, Volumes I, II, and III, 1997 (F. M. Ausubel ed.); Sambrook et al., 1989, *Molecular Cloning: A Laboratory Manual*, Second Edition, Cold Spring Harbor Laboratory Press, Col Spring Harbor, N.Y.; DNA *Cloning: A Practical Approach*, Volumes I and II, 1985 (D. N. Glover ed.); *Oligonucleotide Synthesis*, 1984 (M. L. Gait ed.); *Nucleic Acid Hybridization*, 1985, (Hames and Higgins); *Transcription and Translation*, 1984 (Hames and Higgins eds.); *Animal Cell Culture*, 1986 (R. I. Freshney ed.); *Immobilized Cells and Enzymes*, 1986 (IRL Press); Perbas, 1984, *A Practical Guide to Molecular Cloning*; the series, *Methods in Enzymology* (Academic Press, Inc.); *Gene Transfer Vectors for Mammalian Cells*, 1987 (J. H. Miller and M. P. Calos eds., Cold Spring Harbor Laboratory); and *Methods in Enzymology* Vol. 154 and Vol. 155 (Wu and Grossman, and Wu, eds., respectively).

According to the present invention, stable eukaryotic cells expressing proteins of interest are produced by transfecting the cells with two episomes. An "episome" as used herein refers to an extrachromosomal DNA moiety or plasmid that can replicate autonomously when physically separated from the chromosomal DNA of the host cell. Each episome employed in the method and compositions of the invention contains (i) an Epstein Barr Virus-derived origin of replication (EBV oriP); and (ii) a gene encoding a protein to be expressed. The eukaryotic cells that are transfected express an EBNA 1 protein, the gene for the EBNA 1 protein being stably expressed either chromosomally or from an episome. The gene is preferably contained in a eukaryotic expression cassette. To allow easy manipulation in prokaryotes, the episomes preferably contain a bacterial origin of replication and an antibiotic selectable marker.

It has been determined that separate episomes, each containing an EBV origin of replication, and a gene desired to be expressed, can be transfected into eukaryotic cells to obtain stable transformants that express the genes on both episomes to obtain high RNA transcript levels, and high protein levels. Surprisingly, both episomes have been found to be maintained in high copy numbers. Furthermore, the integrity and copy number of both episomes are stably maintained for extended periods of time without substantial rearrangement of episomal DNA that would interfere with gene expression.

In addition, it has been determined that these advantageous characteristics are maintained even when more than two episomes are transfected in host eukaryotic cells.

The invention therefore allows rapid generation of highly stable cell lines expressing genes on separate episomes in a very short period of time. The cumbersome and lengthy clonal selection techniques required for classical recombination to express multiple genes are eliminated, and the efficiency of successful transfection is comparatively very high.

It has been determined that protein expression is exceedingly reliable using the invention. For example, cells transfected under very different conditions have been found to express the same, or similar, levels of protein when stability has been achieved after a short time, e.g., 2 to 3 weeks.

Furthermore, the method of the invention is highly adaptable, allowing episomes to be easily constructed to contain any desired genes, and easily co-transfected into many differing types of cells.

In one embodiment of the invention, a eukaryotic expression cassette in one episome contains a sequence encoding an EBNA 1 protein that permits replication in the host cell of episomes containing an EBV-derived origin of replication. A second episome contains a sequence encoding the gene of interest. In another embodiment, the episome having the EBNA 1 protein expression cassette contains a second eukaryotic expression cassette. In these embodiments, the episome that does not contain the EBNA 1 protein-encoding expression cassette preferably contains a selectable marker gene for eukaryotic cells. Optionally, the episome that contains the EBNA 1-encoding expression cassette may also contain a selectable marker gene for eukaryotic cells.

The present invention can be used to transform eukaryotic cells with genes encoding proteins of interest, i.e., proteins desired to be expressed by the cells. In one embodiment, the present invention is used to transfect cells in gene therapy applications, e.g., as part of in vivo or ex vivo gene therapy. This use of the present invention overcomes the lack of persistence of gene expression encountered in conventional gene therapy methods of transfection. In this embodiment, episomes are transfected into a patient's cells, e.g., in vitro using methods such as those further described below. The cells can then be cultured in selective media to obtain stably transfected recombinants that persistently express the gene of interest. The stably transfected cells can then be reinfused into the patient. Continuous transcription and translation of EBNA 1 in the transfected cells, particularly from a strong promoter, allows the cells to episomally maintain any desired DNA construct containing the EBV origin of replication in a stable manner.

It is possible, for example, in such an application, to introduce the episomes in vivo (or if desired in vitro) using one or more viral vectors capable of transforming cells in gene therapy to express episomal plasmids. Such viral vectors and their use are described in Viral Vectors: *Gene Therapy and Neuroscience Applications,* 1995 (M. G. Kaplitt and A. D. Loewy eds. Academic Press Inc.), *Adeno-Associated Virus* (Aav): *Vectors in Gene Therapy,* 1996 (K. I. Berns and C. G. Piraud eds. in Current Topics in Microbiology and Immunology, Vol 218), and *Gene Therapy Protocols* (*Methods in Molecular Medicine*), 1996 (P. D. Robbins ed. Humana Press).

Any suitable EBV origin of replication DNA sequence can be employed in the episomes used in the present invention. An example of a suitable EBV origin of replication sequence (oriP) is disclosed in Genbank locus "GB:EBV" (modification date Oct. 29, 1996). The oriP spans the sequence from nucleotide 7337 to the natural HpaI restriction site at nucleotide 9137 in this Genbank sequence. FIG. 3 shows the nucleotide sequence of a suitable EBV oriP, contained within nucleotides 8146–9946 of pCEP4 (commercially available from Invitrogen, Carlsbad, Colo.). This sequence includes the family of repeats (first bolded region in FIG. 3) and the region of dyad symmetry (second bolded region in FIG. 3), which are required for oriP function. EBV oriP sequences that can be used in the invention include those containing modifications from naturally occurring sequences, such as those containing deletions, insertions, substitutions and duplications, of native sequences. Such derivative sequences are obtainable, for example, by maintaining the known regions described above that are required for oriP function. Also, conservative substitutions are well known and available to those in the art. The oriP sequence employed is one that functions effectively in the host cell to direct the replication of the episome in which the oriP sequence is found in the presence of a sufficiently high amount of an EBNA 1 protein.

Figure 2D:
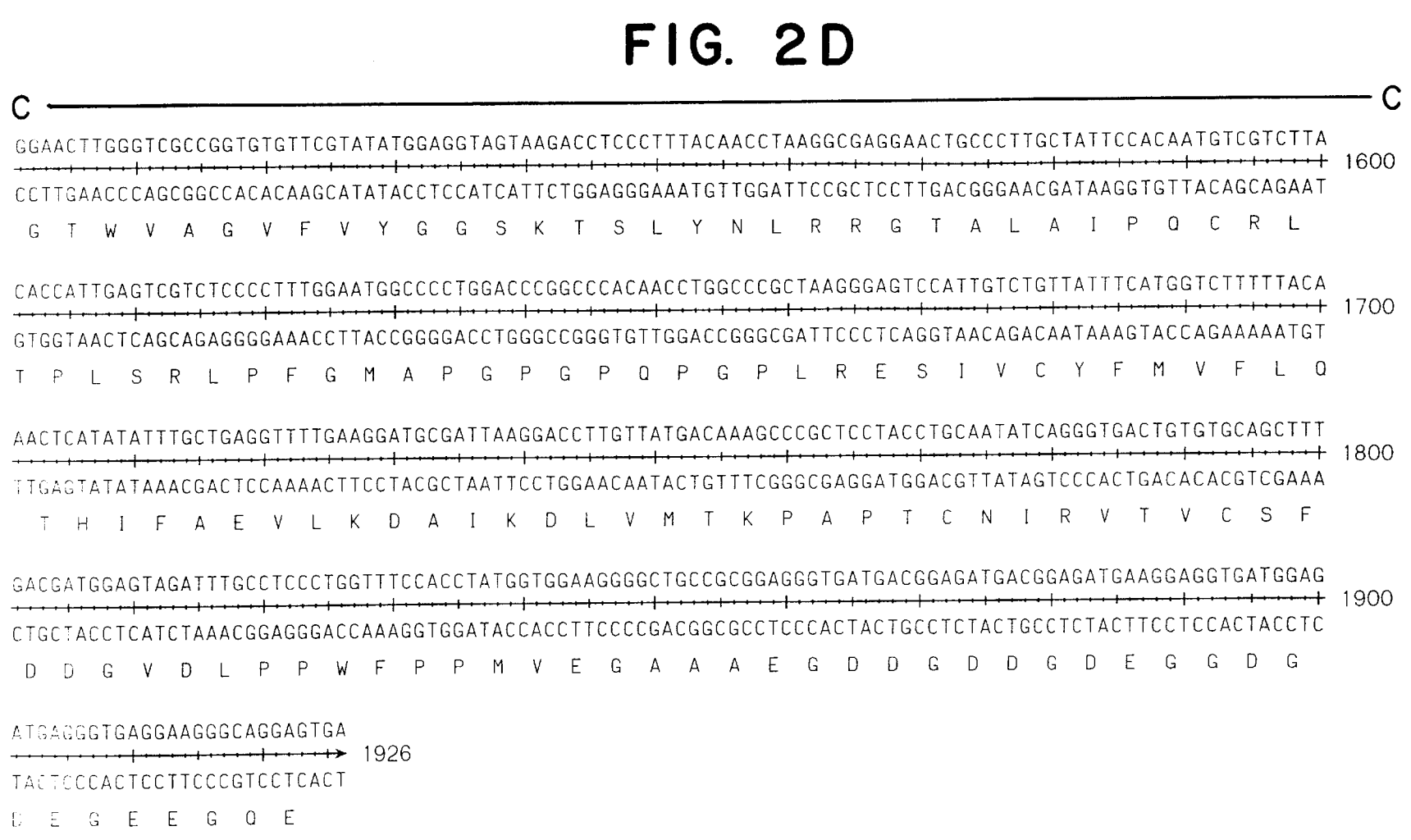

DNA encoding any suitable EBNA 1 protein can be expressed by the transfected cells. An example of EBNA 1-encoding DNA is shown in FIG. 2. EBNA 1-encoding DNA is available from Invitrogen, Inc. (Carlsbad, Calif.) and is contained in several of its commercially available EBV series plasmids, including pCMVEBNA, catalog number V200-10. The sequence of the anti-sense strand of pCMVEBNA is shown in FIG. 1. The EBNA open reading frame shown in bold letters, includes bases 2421 to 496. The stop and start codons are underlined. DNA sequences encoding truncated versions of EBNA 1 (including, e.g., those commercially available from Invitrogen such as pREP7 or pREP10 under catalog numbers V007-50 and V010-50, respectively) are well known and can be used to encode the EBNA 1 protein. Furthermore, DNA encoding the EBNA protein can encode variants of the naturally occurring EBNA 1 amino acid sequence, including those containing, e.g., deletions, insertions, or substitutions, wherein the expressed protein supports replication of EBV oriP-containing episomes in the host cell.

Furthermore, degenerative DNA sequences that encode the same EBNA 1 protein can be employed. Degenerative DNA sequences capable of expressing the same amino acid sequence are well known in the art, as are methods of constructing and expressing such DNA sequences.

Eukaryotic expression cassettes included in the episomes preferably contain (in a 5'-to-3' direction) a eukaryotic transcriptional promoter operably linked to a protein-coding sequence, splice signals including intervening sequences, and a transcriptional termination/polyadenylation sequence. Promoters suitable for use in EBNA 1-encoding episomes of the invention are those that direct the expression of the DNA encoding the EBNA 1 protein to result in sufficient steady-state levels of EBNA 1 protein to stably maintain EBV oriP-containing episomes.

Strong promoters are preferred for use in the invention. A "strong promoter" is one which results in a net steady-state concentration of RNA approximately 0.25 times the steady-state level of GAPDH or greater. The following formula can be used to determine promoter activity in most cell types: promoter activity is acceptable if (RNA concentration of episomally derived gene)/(GADPH steady state RNA) $\geq 0.25$. Alternatively, if GAPDH is present in exceptionally low quantities in a given cell type, the steady-state concentration of beta actin can be substituted instead. This formula takes into account the number of episomes that may be present within the cell, which normally varies between about 1 and 60 copies (Margolskee et al., *Curr. Topics in Microb. and Immunol.* 158, 67–95, 1992; Yates et al., *Nature.* 313:812–815, 1985.).

Non-limiting examples of such "strong promoters" include early or late viral promoters, such as, e.g, SV40 early or late promoters, cytomegalovirus (CMV) immediate early promoters, Rous Sarcoma Virus (RSV) early promoters; eukaryotic cell promoters, such as, e.g., beta actin promoter (Ng, S.Y., *Nuc. Acid Res.* 17:601–615, 1989, Quitsche et al., *J. Biol. Chem.* 264:9539–9545, 1989), GADPH promoter (Alexander et al., *Proc. Nat. Acad. Sci. USA* 85:5092–5096, 1988, Ercolani et al., *J. Biol. Chem.* 263:15335–15341, 1988), metallothionein promoter (Karin et al. *Cell* 36: 371–379, 1989; Richards et al., *Cell* 37: 263–272, 1984); and concatenated response element promoters, such as cyclic AMP response element promoters (cre), serum response element promoter (sre), phorbol ester promoter (TPA) and response element promoters (tre) near a minimal TATA box. It is also possible to use human growth hormone promoter sequences (e.g., the human growth hormone minimal promoter described at Genbank, accession no. XO5244, nucleotide 283–341) or a mouse mammary tumor promoter (available from the ATCC, Cat. No. ATCC 45007).

Transcription termination/polyadenylation sequences include without limitation those derived from the thymidine kinase (tk) gene or SV40-derived sequences, such as found, e.g., in the pCEP4 vector (Invitrogen).

Selectable marker genes for use in the episomes employed in the invention are genes that encode proteins conferring resistance to specific antibiotics and/or factors that allow cells harboring these genes to grow in the presence of the cognate antibiotics or factors. Non-limiting examples of eukaryotic selectable markers include antibiotic resistance genes conferring resistance to hygromycin (hyg or hph, commercially available from Life Technologies, Inc. Gaithesboro, Md.); neomycin (neo, commercially available from Life Technologies, Inc. Gaithesboro, Md.); zeocin (Sh Ble, commercially available from Pharmingen, San Diego Calif.); puromycin (pac, puromycin-N-acetyl-transferase, available from Clontech, Palo Alto Calif.), ouabain (oua, available from Pharmingen) and blasticidin (available from Invitrogen).

Non-limiting examples of selectable marker genes for use in bacteria include antibiotic resistance genes conferring resistance to ampicillin, tetracycline and kanamycin. The tetracycline (tet) and ampicillin (amp) resistance marker genes can be obtained from any of a number of commercially available vectors including pBR322 (available from New England BioLabs, Beverly, Mass., cat. no. 303-3s). The tet coding sequence is contained within nucleotides 86–476; the amp gene is contained within nucleotides 3295–4155.

The nucleotide sequence of the kanamycin (kan) gene is available from vector pACYC 177, from New England BioLabs, Cat no. 401-L, GenBank accession No. X06402.

The episomes can encode a reporter gene, such as a luciferase gene. Examples of DNA sequences encoding luciferase genes are described by Wood et al., *Science* 244:700–702, 1989; Zenno et al., U.S. Pat. No. 5,618,772; and *Proc. Natl. Acad. Sci. USA,* 82:7870–7873, 1985. Reporter genes that can also be used include green fluorescent protein (GFP, Clontech, Cat. No. 60771), secreted alkaline phosphatase (SEAP, pSEAP2-Basic, Clontech, Cat. No. 6049-1), growth hormone (which can be measured by ELISA), chloramphenicol acetyl transferase (CAT, available from Promega, Madison, Wis., pCAT(Tm)-3-Basic Vector Cat. No. E1041), beta-lactamase, and beta-galactosidase.

Elements can be coded for in an episome that respond to transduction signals. Cre elements (a 6-fold repeat of cyclic AMP response elements available from Stratagene in phagemid vector pCRE-Luc, Cat. No. 219076) were used in experiments described below to respond to changes in intracellular cAMP concentrations. Alternately, serum response elements (SRE, Stratagene phagemid vector pSRE-Luc. Cat. No. 219080), nuclear factor kB (NF-kB, Stratagene phagemid vector pNFKB-Luc Cat. No. 219078), activator protein 1 (AP-1, Stratagene phagemid vector pAP-1-Luc, Cat. No. 219074) and serum response factor elements (Stratagene phagemid vector pSRF-Luc, Cat. No. 219082), can be encoded.

The episomes that are transfected according to the method of the invention may be transfected sequentially, simultaneously, or substantially simultaneously (i.e., prior to clonal selection). Although it is possible to reproducibly transfect two and three episomes at the same time into cells, to ensure the greatest cell survival rate it is preferred to transfect the episomes sequentially, e.g. one per week. In a particularly preferred embodiment, an episome containing the EBNA 1 gene is introduced first.

"Transfection" as used herein refers to the introduction of DNA into a host cell. Any appropriate transfection method can be used, including without limitation calcium phosphate co-precipitation, electroporation, or lipofection using cationic lipids. These techniques are well known to those of ordinary skill in the art.

Using calcium phosphate precipitation, between about 4 and 20 $\mu$g of each episome is typically used to transfect between about 0.75 to $1.5 \times 10^6$ cells in a T75 flask or 10 cm dish. The amounts of episome and the number of cells used, however, can vary depending on the particular episomes and cells employed. Following transfection of the final episome used, cells are preferably incubated in selective media for about two weeks at which time protein expression has usually stabilized. Cells are preferably maintained under selective pressure to prevent loss of the episomes, which generally occurs at a rate of between about 2 and 5% per generation in the absence of selection.

It has been determined that transfection with two or more episomes according to the invention produces cell lines that are stably transfected. The method of the invention preferably is employed to produce episomally co-transfected cell lines that remain stably transfected for at least about five months after transfection. Stability of transfection may be determined by detection of (i) extrachromosomal plasmid DNA and/or (ii) expression of the gene(s) of interest (as reflected in steady-state mRNA levels or in the protein product(s)). For an embodiment of the invention described in the Examples section below, it has been determined using genomic Southern blotting techniques that over a period of 3 weeks the number of episomes per cell stabilized at approximately eight copies per cell.

Any eukaryotic cells which support stable replication of the plasmids described above may be used in practicing the invention. Non-limiting examples of host cells for use in the present invention include HEK 293 cells (American Type Culture Collection, Manassas, Va. (ATCC) Deposit Number CRL-1573, referred to below as "293 cells"), CVIEBNA cells (ATCC CRL10478), Hela cells, D98/raji cells, 293EBNA (also known as 293E) available from Invitrogen, Cat. No. R62007, CVI cells (ATCC Cat. No. CCL 70) and 143 cells. In addition, primary cultures of eukaryotic cells, such as bone marrow stem cells or liver cells, may be isolated from their tissue of origin and transfected with the episomes according to the invention. In vivo transfection of cells to express more than one episome using suitable vectors, such as viral vectors used in gene therapy, can also be carried out.

Episomes can be employed in the invention to transfect primate or canine cells. EBNA 1 can be stably transfected into any primate or canine cell using well known techniques, and the resulting cell line that expresses EBNA 1 from an integrated gene copy can be used to support replication of multiple episomes. Alternately, a cell line that already harbors infectious or defective EBV can be used, as long as EBNA 1 is expressed. This includes many EBV transformed lymphoblasts available from the ATCC. As discussed above, it is also possible to express EBNA 1 from a stably transfected episome.

By applying the method of the present invention, episomes can be used to immortalize cells using, e.g., genes encoding well known immortalization antigens. For example, in one embodiment of the invention, cells can be immortalized by SV40 T antigen that is encoded by DNA contained in one transfected episome. If desired, the gene encoding the immortalization antigen can be present in the same episome containing DNA that encodes an EBNA 1 antigen. Primary cells in culture can then be immortalized by transfection with episomes according to the methods described above and methods described more particularly in Gonos et al. *Mol. Cell. Biol.* 16:5122–5138, 1996; and Ikran et al., *Proc. Nat'l. Acad. Sci. USA* 91:6444–6542, 1994. The use of an episome encoding an antigen effective to immortalize cells, such as SV40 T antigen, allows transfection of multiple episomes in primary or non-immortalized cells derived from primate or canine sources. In addition to T antigen, many other genes that confer an immortalized phenotype are well known and available, including the E6 and E7 genes of human papilloma virus (HPV)-16 (Rhim et al., *Carcinogenesis.* 19:673–681, 1996), and oncogenes such as ras (Rovinski and Benchimol, *Oncogene.* 5:445–452, 1988) and myc (Brodeur, *Adv. Pediata* 34:1–44, 1987).

SV40 T antigen sequences for use in the present invention can be retrieved from the Genbank database by using Locus=SV40 CO, or accession numbers JO2400, JO2403, JO2406, JO2407, JO2408, JO2409, JO24101, JO4139, M24874, M24914, M28728, or V01380. The Genbank database provides the sequence of the SV40 complete genome. An SV40 genomic clone, pBRSV, is available from ATCC, Cat. No. 450190. The complete T antigen sequence is disclosed in Fiers, W. et al., *Nature* 273: 113–120, 1978.

In one embodiment of the present invention, cells are transfected with three or more episomes. Using this method, a recombinant cell is produced that expresses a plurality of proteins. The method involves, for example, transfecting a host cell with (a) a first episome comprising an EBV origin of replication (OriP) and a gene encoding a first protein; (b) a second episome comprising the EBV OriP, and a gene encoding a second protein, and (c) a third episome comprising the EBV OriP and a gene encoding a third protein of interest. In one embodiment, the first episome encodes an EBNA 1 protein, and the second and third episomes also encode (in addition to encoding proteins desired to be expressed, such as, e.g., receptor sub-units, or channel sub-units) first and second selectable markers for eukaryotic cells. In one aspect of this embodiment, the second or third episome also contains a reporter gene. An example of this embodiment is further described below. In this embodiment, the triply (or more) transfected cells are incubated in media wherein only cells expressing the EBNA 1 gene and the first and second selectable marker genes survive. The triply-transfected cells can then be recovered.

In this embodiment, transfection and concomitant expression of multiple genes can advantageously be carried out to establish cell lines expressing several genes at once in a short period. It has been found possible, for example, to obtain such cell lines in as little as three weeks. Screening of clonal cell populations is not required and pooled populations of transfected cells can be used.

Transfection of cells to express multiple genes according to the invention can be used with any desired combination of genes. The invention is particularly useful with respect to transfection of genes encoding receptors, transporters, ion channels or adhesion molecules.

For example, many receptors, transporters, adhesion molecules and ion channels are composed of multiple subunits which must be present in stoichiometric quantities for functional activity. Examples include receptors containing two different subunits that can be encoded on multiple episomes, such as the insulin receptor, interleukin receptors (e.g., IL3R, IL4R, IL5R, IL6R, IL11R, IL12R, IL13R), OBR (leptin receptor), and TGFbR (transforming growth factor β receptor). Examples also include moieties composed of three different subunits, such as LIFR (leukemia inhibitory factor receptor), IL2R, CNTFR (ciliary neurotrophic factor receptor) and those composed of five different subunits, such as Na+/K+ transporters, NMDA (N-methyl D-aspartate) receptors, voltage-gated Na+ channels, and nicotinic acetyl choline receptor channel complex. Examples of such receptors, transporters and ion channels are described in Kandel et al., *Principles of Neutral Science,* Third Ed. Norwalk, Conn., Appleton & Lange, 1991.

One example of transfection of multiple genes according to the invention, described in detail below, involves transfection of a G protein coupled receptor (GPCR), its preferred G protein alpha subunit (Gαi2), and a reporter plasmid responsive to signal transduction.

The method of the invention can also be used to cause a cell to express any desired combination of signal transduction effectors in the GPCR pathways, including expression of any of Gα, Gβ, Gγ subunits, a phospholipase isozyme such as PLCβ, or a protein kinase such as phosphokinase C (PKC). Expression of such effectors can enhance signal transduction responses by increasing the intracellular concentrations of rate-limiting enzymes.

It is also possible, for example, to obtain cells useful in a tyrosine kinase receptor assay that do not have a hematopoietic lineage. To do this, the desired host cells are transfected using the method of the invention with episomes encoding the two subunits (jak and stat) of the tyrosine kinase receptor of interest. The host cells can also be transformed with a construct containing stat response elements that drive transcription of a reporter gene. DNA sequences encoding these subunits and response elements are well known.

It is also possible, using the method of the invention, to transfect desired host cells with episomes containing DNA encoding genes of a tyrosine kinase cascade, such as the Ras-Raf-Mek-MAPK cascade. DNAs encoding these genes are known and readily available.

It is also possible to express several targets, e.g., receptors that are targets of a drug discovery program, in the same cell at the same time. This allows performance of two or more screening experiments at once. It also allows experiments to be conducted in which the experimental target and a control target are present in the same sample.

The method of the invention can also be used to identify protein-protein interactions as a mammalian counterpart to the yeast two-hybrid system.

When practicing the method of the invention, episomes can be transfected in order to change the phenotype of the host cell. For example, if it is desired to change the phenotype of a weakly adherent cell line to an adherent phenotype, a macrophage scavenger receptor can be added on a separate episome (Robbins and Horlick, 1998). Alternatively, as described above, an immortalizing gene, such as a gene encoding SV40 T-antigen, or papilloma virus E6 and E7 genes can be transfected episomally.

In one embodiment, the recombinant cell lines of the invention containing multiple episomes are used in assays to identify drug candidates. Compounds assayed can be derived from combinatorial libraries on polymer beads. For example, library compounds can be eluted from the beads and evaporated to dryness in microliter plates in preparation for an assay using the cells. Compounds on beads can be released by photocleavage, or another type of cleavage. Cleavage of photocleavable linkers is preferred. Such linkers, and methods for their cleavage, are described in Barany et al. (1985) *J. Am. Chem. Soc.* 107:4936. Examples of other linkers and the relevant cleavage reagents are described in WO 94/08051.

Using combinatorial libraries prepared on beads, the identity of active compounds is preferably determined using the encoding system described in U.S. Pat. Nos. 5,721,099 and 5,565,324. In this system, chemical tags encoding the identities of the compounds are applied to the solid supports. The identity of the compound on a given support can be determined by detaching the chemical tags from the support, identifying the tags by, e.g., gas chromatography, and correlating the identities of tags with the identity of the compound. Once an active compound is identified, the corresponding bead (which had contained the compound) can be examined, and the identity of the compound determined by releasing the tags and decoding by this method.

It is possible to carry out fluorescent assays using the cells in a high throughput assay employing confocal microscopy to detect the amount of fluorescence bound to individual cells. Such assays are described in U.S. application Ser. No. 08/868,280, filed Jun. 3, 1997.

The present invention is described below in working Examples which are intended to further describe the invention without limiting the scope.

EXAMPLE 1

Construction of Episomal Expression Vectors

Construction of pHEBO Vector

The pHEBo vector was made using commercially available vectors. The sequence of vector pBR322 (Genbank accession number synpbr322) from nucleotide 1 to nucleotide 772 was ligated to the nucleotide sequence of vector pCEP4, FIG. 3, from position 8146 to 10376 (Invitrogen, Cat. No. V004-50). To this construct was ligated pCEP4 nucleotides 1333 to 5500. Prior to ligation, fragments were PCR amplified or joined using preexisting restriction sites. The resulting plasmid contained the Epstein Barr Virus (EBV) origin of replication (oriP), a hygromycin resistance marker (hyg) transcribed from the minimal Herpes Simplex Virus (HSV) thymidine kinase (tk) promoter, and was terminated with the tk poly adenylation signal (poly(A)), in vector pBR322. The pHEBo vector is shown schematically in FIG. 4.

Construction of pcmvmcs1 Vector

Vector p394 was constructed according to Colberg-Poley, A. M. et al. *J Virol.* 1992 January; 66(1): 95–105. Briefly, the vector can be made by cloning the 658 bp CMV IE promoter (which can be obtained from vector pCEP4, nucleotide 1132 to 474) into the EcoRV site of pBSIISK(+). Oligonucleotides 5'-ATATCATAATATGTACATTTATATTG-3' (SEQ ID NO:4), and 5'-TCGCGACGTCTCCGTGTAGGCGATCTGACGGTTCACTAAAC-3' (SEQ ID NO:5), were used to amplify the promoter by PCR.

The SV40 poly(A) signal, which can be obtained, e.g., from pCEP4, (from the native BsaBI site at nucleotide 176 to the native BamHI site at position 412) was cloned into the SmaI and BamHI sites of pBSSK(+)-CMVIE. Using the remaining EcoRI and PstI sites in between the CMV promoter and SV40 poly(A), a multicloning site was added using oligonucleotides:

5'-AATTCGCGACGCGTGATATCTGCAGGCCTAGATCTCTAGATAAGTAATGATCATGCA-3' (SEQ ID NO:6), and
5'-TGATCATTACTTATCTAGAGATCTAGGCCTGCAGATATCACGCGTCGCG-3' (SEQ ID NO:7), yielding vector p394.

Figure 5:
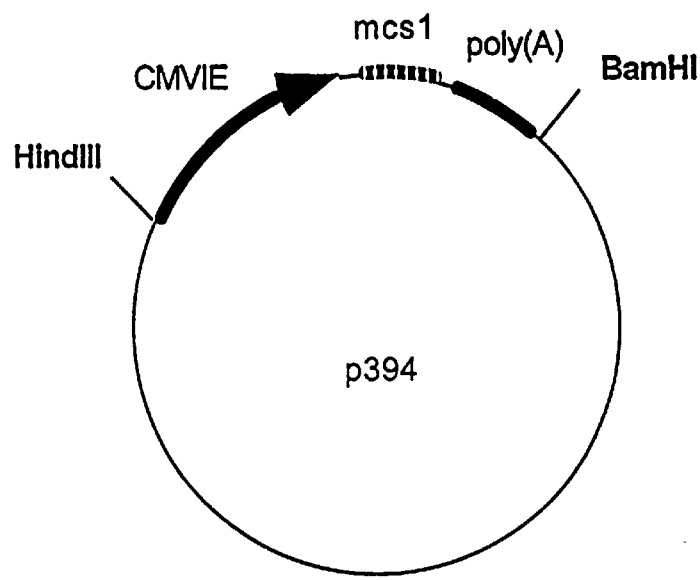
FIG. 5 is a schematic diagram showing the vector p394.
Figure 6:
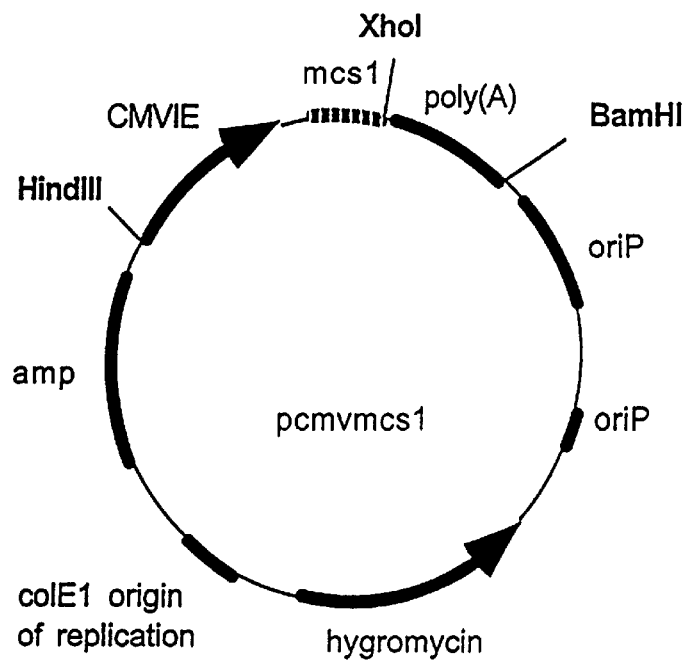
FIG. 6 is a schematic diagram of plasmid pcmvmcs1.

Vector p394 (FIG. 5), was cleaved with HindIII and BamHI to yield a 1.3 kb HindIII-BamHI fragment containing the cytomegalovirus immediate early promoter (CMV), a multicloning site region (mcs), and the SV40 poly(A) region. This fragment, which comprises an "expression cassette" was cloned into the HindIII and BamHI sites of pHEBo to yield pcmvmcs1 (FIG. 6). The mcs contains the following restriction enzyme sites: Esp3I, EcoRI, NruI, Ml uI, EcoRV, PstI, StuI, BglII. The mcs in vector pcmvmcs1 was replaced with the following sites: Esp3I, AgeI, StuI, KpnI, AvrII, XhoI, by a synthetic oligonucleotide linker that contained overhangs compatible with the Esp3I and BglII sites. The BglII site was not recreated by the oligonucleotide linker. This vector was designated pcmvmcs3.

Construction of pm3ar Vector

Figure 7:
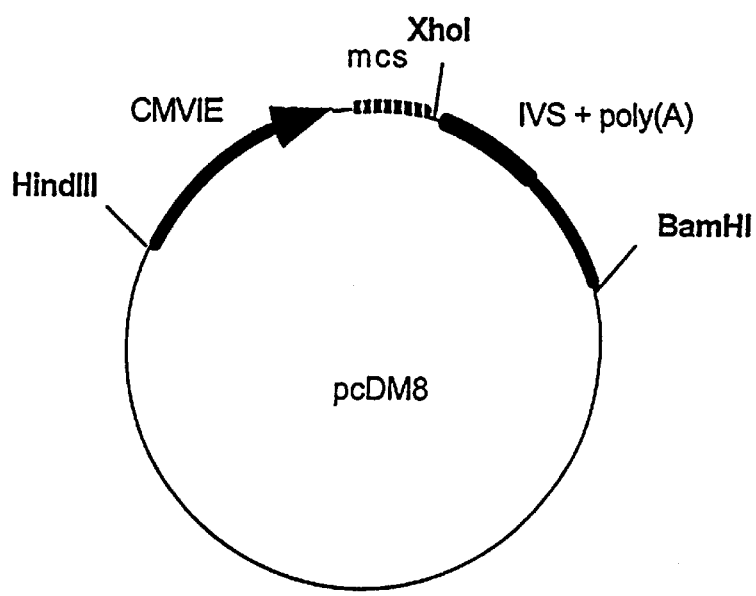
FIG. 7 is a schematic diagram of vector PCDM8.
Figure 8:
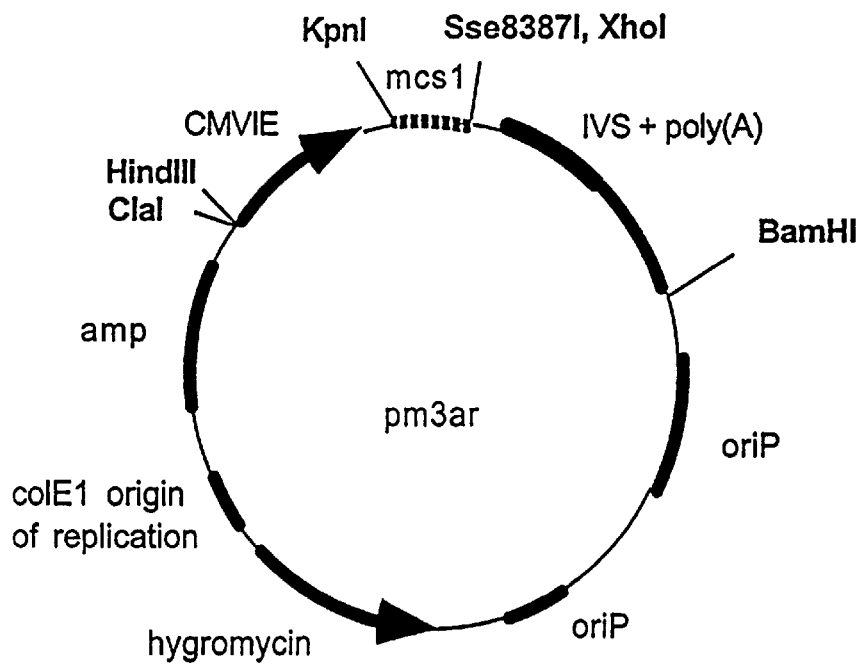
FIG. 8 is a schematic diagram showing vector pm3ar.

An intron (called IVS or "intervening sequence") was added to the expression cassette (defined herein as the CMVIE-mcs-poly(A) containing nucleotides) as follows. An XhoI-BamHI fragment containing the SV40 early intron and poly(A) signals was excised from vector pCDM8 (Invitrogen, Carlsbad, Calif.; FIG. 7). The poly(A)-containing fragment was removed from vector pcmvmcs3 by digestion with restriction enzymes XhoI and BamHI, and the XhoI-BamHI fragment from pCDM8 was added, generating vector pm3ar (FIG. 8).

CCR3 Expression Vector

Figure 9:
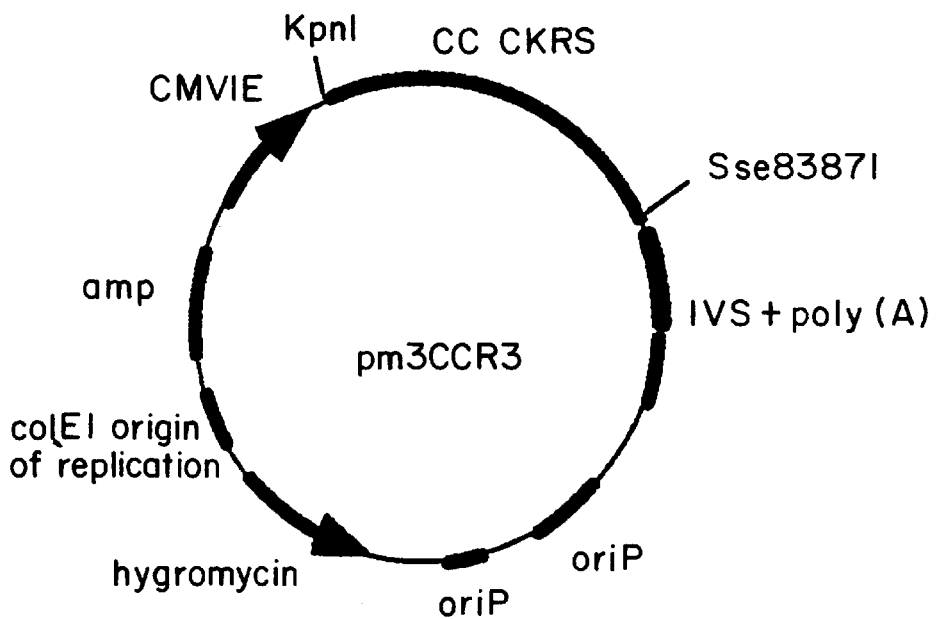
FIG. 9 is a schematic diagram showing vector pm3CCR3.

An episomal vector which codes for the C-C chemokine receptor 3 ("CCR3") was constructed. The coding region for the receptor was obtained by PCR amplification of genomic DNA, using the oligonucleotide 5'-GTGAAATGACAACCTCACTAGATACAG-3' (SEQ ID NO:8), as the sense primer, and 5'-CTGACCTAAAACACAATAGAGAGF-3' (SEQ ID NO:9), as the antisense primer. The PCR fragment obtained was cloned into the EcoRV site of pBSIISK; a Bluescript vector commercially available from Stratagene, La Jolla, Calif., Stratagene Cat. No. 212205, Genbank accession number 52325. The coding region was excised from pBSIISK+ using the restriction enzymes SpeI and NsiI, and the fragment containing DNA coding for CCR3 was cloned into the AvrII and Sse8387 I sites of vector pm3ar (FIG. 8) to generate episomal expression construct pm3CCR3 (FIG. 9).

Figure 10A:
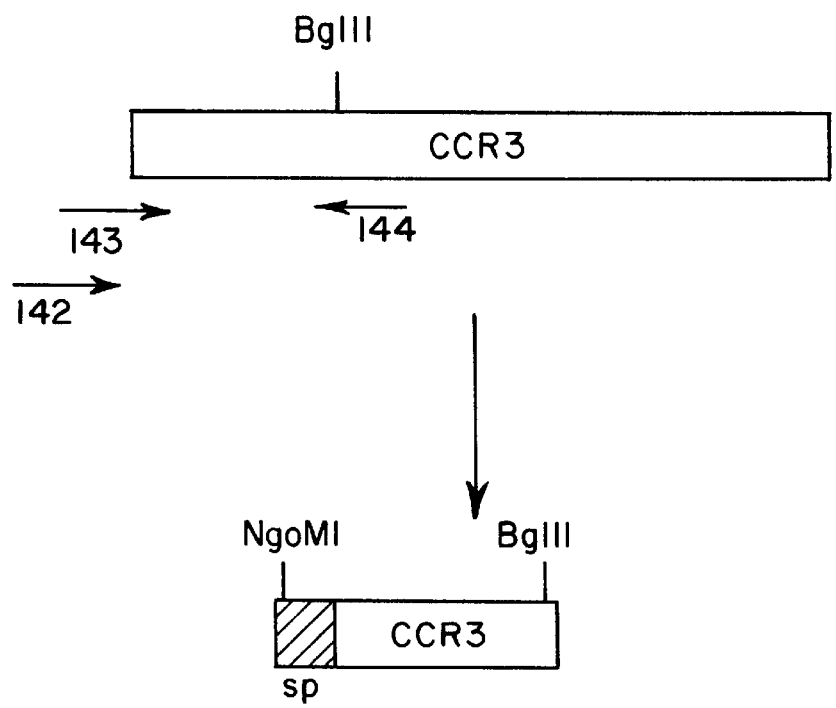
FIG. 10 is a schematic diagram showing expression vector pm3CCR3sp.
Figure 10B:
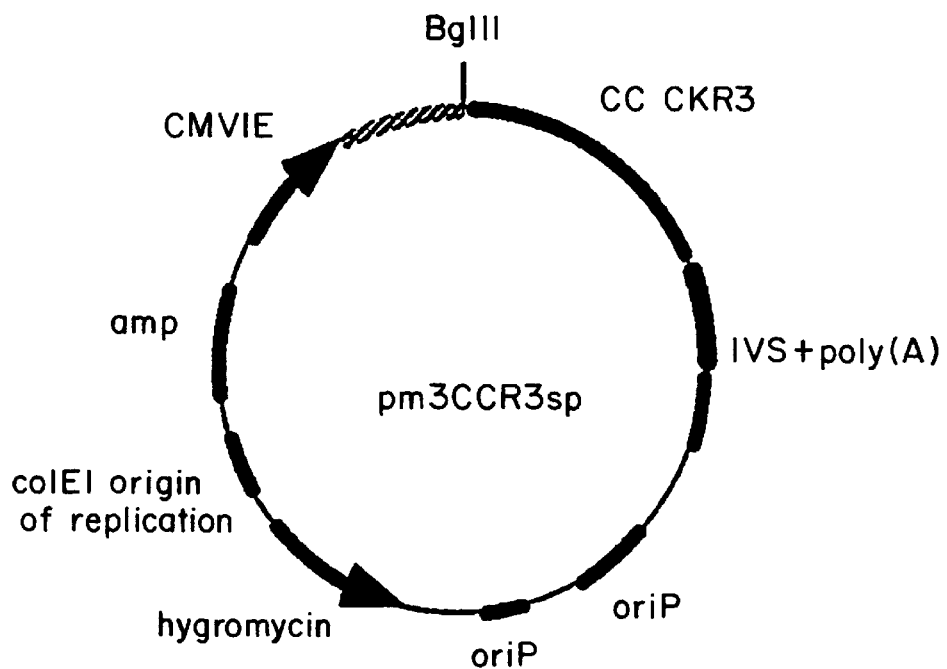

A hydrophobic signal sequence was added to the CCR3 coding sequence by PCR. Vector pm3CCR3 was used as a template and oligonucleotide 144, 5'-TGTCGATTGTCAGCAGGATTATG-3' (SEQ ID NO:10) (which begins at nucleotide +390 and maps 3' to the unique BglII restriction site on the vector) and oligonucleotide 143,5'GTTCTGTCTCTGCTGCCACTGCTCGAGGCTCAAACAACCTCACTAGATACAGTTGAG-3' (SEQ ID NO:11) (which overlaps the CCR3 coding sequence and contains a long tail encoding approximately two-thirds of the hydrophobic signal sequence) were used as primers. The resulting 428 base pair fragment was then used as a template for PCR, using oligonucleotide 144 and oligonucleotide 142, GAGCAGCCGGCACCACCATGGCTCT-GTCTTGGGTTCTGACTGTTCTGTCTCT-GCTGCCACTG (SEQ ID NO:12) (which encodes the remainder of the hydrophobic signal sequence and contains a Kozak consensus sequence for efficient initiation of translation). The resulting 461 base pair fragment was digested with NgoMI and BglII and cloned into the AvrII and BglII sites of pm3CCR3 to generate expression vector pm3CCR3sp (FIG. 10).

Construction of pE3 Vector

Figure 11:
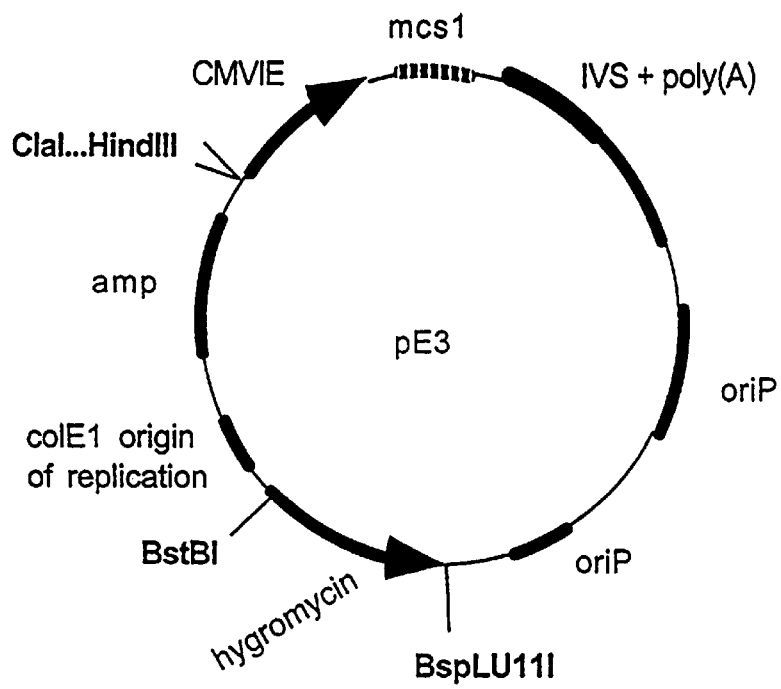
FIG. 11 is a schematic diagram of vector pE3.

Vector pm3ar (FIG. 8) was altered to provide an additional set of cloning sites immediately upstream from the CMVIE promoter. The new sites were added using a synthetic oligonucleotide linker 5'-CGATCACGTGCAGCTGAGATCTA-3' (SEQ ID NO:13) that contained the restriction sites, ClaI, AscI, BssHII, PacI, HindIII and overhangs compatible with the ClaI and HindIII sites of pm3ar. The new vector was designated pE3 (FIG. 11).

Construction of pE3delta Vector

Figure 12:
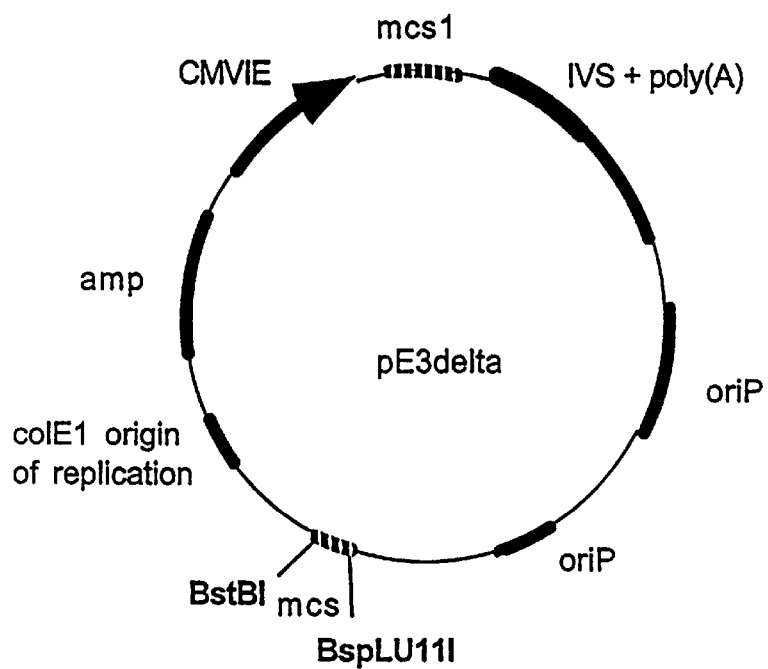
FIG. 12 is a schematic diagram showing vector pE3delta.

Vector pE3delta (FIG. 12) was generated by the digestion of vector pE3 with BstBI and BspLU11I to remove the hygromycin coding region. The hygromycin coding region was replaced with a synthetic oligonucleotide linker 5'-CATGTAGATCTCAGCTGCACGTGAT-3' (SEQ ID NO:14) containing the multiple cloning sites BglII, PvuII and PmlI.

Construction of pE3pur Vector

Figure 13:
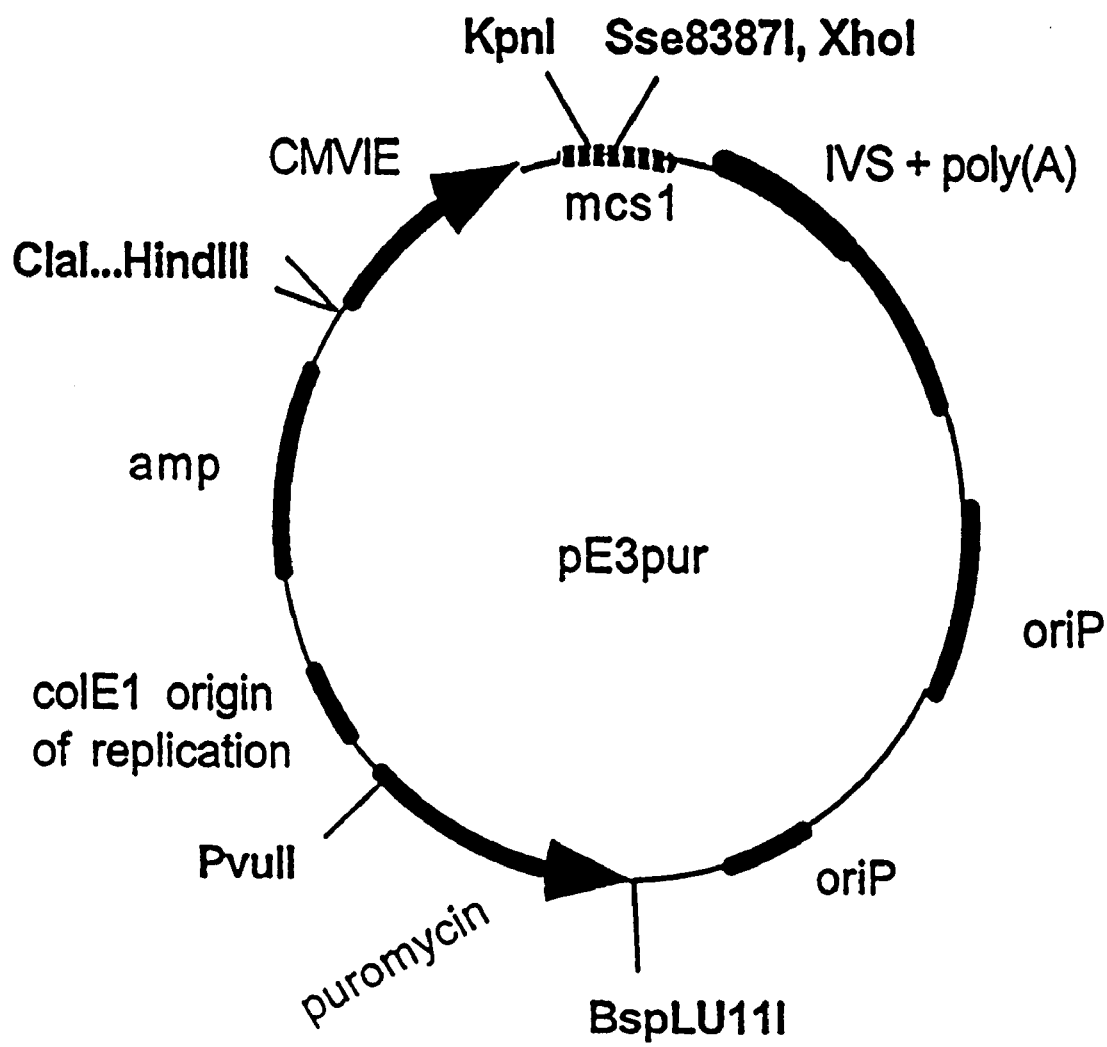
FIG. 13 is a schematic diagram showing vector pE3pur.

Vector pE3pur (FIG. 13) was constructed by the digestion of vector pE3delta with PvuII and BspLU11I followed by ligation to a PvuII-BglIII fragment obtained from vector pPur (Clontech, Cat. No. 6156-1, Genbank accession number U07648). The PvuII-BglIII fragment from vector pPur contains the SV40 promoter, a puromycin resistance gene, and an SV40 poly(A) tail.

$G_{i\alpha 2}$ Expression Vector

Vector pBN31, which contains the wildtype sequence for murine $G_{i\alpha 2}$ cloned into the EcoRI site of vector pCDNAI, was obtained from the ATCC, Cat. No. 63311. Vector pE3pur (FIG. 13) was digested with KpnI and XhoI, which correspond to restriction sites found within the multicloning regions at the 5' and 3' ends, respectively, of the $G_{i\alpha 2}$ coding region. The pBN31 vector obtained from the ATCC was also digested with KpnI and XhoI, and a fragment containing the $G_{i\alpha 2}$ coding region was excised. This fragment was cloned into the KpnI and XhoI sites of vector pE3pur, to produce vector pE3purGiα2. This vector was used without further modification to transfect cells.

Construction of pE3purEBNA

The coding region for EBNA 1 was excised from vector pCMVEBNA (Invitrogen, Carlsbad, Calif.;) using restriction enzymes KpnI and Sse8387 I and cloned into the KpnI and Sse8387 I sites of vector pE3pur (FIG. 13) to make construct pE3purEBNA.

Construction of pm3orl 1

The 1110 bp coding sequence for human orphanin receptor type I (orlI) was PCR amplified from whole human brain Quickclone cDNA (Clontech) using the following oligos:

Orl 1. CCCTCTAGACCATGGAGCCCCTCTTCCCCGCGCCG (SEQ ID NO:15)

Orl 2. CCCTCTAGACCAGGCACCATGGGCAGGTCCACGCC (SEQ ID NO:16)

The ATG start codon is underlined in orl 1, and the underlined C in orl 2 is 'G' of the TAG stop codon in the reverse complement strand. Each oligo contains an NcoI site.

The PCR product was digested with NcoI site of Litmus 28 (New England BioLabs, Beverly, Mass.). The fragment containing the orlI coding sequence was then reclaimed from Litmus 28 with AgeI (5' side) and XhoI (3' side) and the resulting 1200 bp fragment was cloned into the AgeI and XhoI sites of vector pE3 (FIG. 11) to make pm3orl1.

Construction of pE3zeocretkluc

Construct pGL2-6xcretkluc (p144) contains a 6-fold repeat of the cyclic AMP (cAMP) response elements (cre), the Herpes virus minimal thymidine kinase (tk) promoter, luciferase (luc) coding sequence (cds) and SV40 IVS (intervening sequence) and poly(A) region. The construction of plasmid p144 was accomplished as follows. Oligos were made based on sequences of 6 cre elements described by Himmler et al. *J Recept. Res.* 13: 79–94, 1993. The 4 pairs were annealed, ligated and cloned into the SacI and BglII sites of vector pGL2-bas (Promega) to make vector pGL2-6xcre. The tk minimal promoter was PCR amplified from vector pE3 using oligos tk1 and tk2. The PCR amplified product was digested with BglII and XhoI and subcloned into the BglII and XhoI sites of construct pgl6xcre to make construct pGL2-6xcretkluc.

```
Pair 1
cre1.  CTccggatcctccttggctgacgtcagtagagagatcccatggc        (SEQ ID NO:17)

cre2.  atctctctactgacgtcagccaaggaggatccggAGAGCT            (SEQ ID NO:18)

Pair 2
cre3.  cgtcatactgtgacgtctttcagacaccccattgacgtcaatgggag     (SEQ ID NO:19)

cre4.  Ttgacgtcaatggggtgtctgaaagacgtcacagtatgacggccatggg   (SEQ ID NO:20)

Pair 3
cre5.  ggtaccgcaccagacagtgacgtcagctgccagatcccatggc         (SEQ ID NO:21)

cre6.  gatctggcagctgacgtcactgtctggtgcggtaccctccca          (SEQ ID NO:22)

Pair 4
cre7.  cgtcatactgtgacgtctttcagacaccccattgacgtcaatgggaga    (SEQ ID NO:23)

cre8.  gatctctcccattgacgtcaatggggtgtctgaaagacgtcacagtatgacggccatgg  (SEQ ID NO:24)

tk1
ttttagatctcagaagccGAATTCGAACACGCAGATGCAG                   (SEQ ID NO:25)

tk2
AAAACTCGAGATTGCGGCACGCTGTTGACGC                            (SEQ ID NO:26)
```

$G_{i\alpha 2}$ coding region was excised. This fragment was cloned into the KpnI and XhoI sites of vector pE3pur, to produce The construct was treated with BamHI methylase (to render all but the desired BamHI site uncleavable). The plasmid was then digested with XmaI and BamHI and the ~3100 bp fragment containing the 6xcre elements, tk minimal promoter, luc coding sequence, SV40 IVS and poly(A+) signals, was cloned into the NgoMI and BglII sites of vector pHEBomcs5 to make vector pE3cretkluc.

pHEBomcs5 was derived from pHEBo (FIG. 1d) by digestion with the unique HpaI site and blunt-end insertion of oligo linkers, ctcgagaagcttggccggccagatctgcggccgcg (SEQ ID NO:27) (and its reverse complement) encodino restriction sites XhoI, HindIII, NgoMI, NaeI, FseI, BglII, and NotI.

Vector pE3cretkluc encodes hygromycin resistance. In order to make a version that encodes zeocin resistance, pE3cretkluc was digested with NotI, this site was blunted in the presence of Klenow polymerase and all 4 dNTPs, and the vector was recut with SacI to liberate a 3.2 kb fragment containing the cretkluc expression cassette. Vector pE3SVzeo was digested with HindIII, this site was also blunted in the presence of Klenow polymerase and all 4 dNTPs, and the vector was subsequently digested with SacI. This permitted the replacement of the CMV promoter from pE3SVzeo with the cretkluc expression cassette to complete vector pSVzeo-cretkluc.

Vector pE3 was digested with Csp45 I and BspLu11I to remove the hygromycin expression cassette. Oligo linkers PUR1 (CGATCACGTGCAGCTGAGATCTA) (SEQ ID NO:28) and PUR2 (CATGTAGATCTCAGCTGCACGTGAT) containing (SEQ ID NO:29) unique Bgl II Pvu II and Pml I sites were annealed and inserted into the Csp45 I and BspLu11I cut vector to make construct pE3deltahyg.

Vector pSVzeo purchased from Invitrogen (cat. no. V502-20) was digested with EcoRV and BamHI and the ~1 kb fragment containing the SV40-zeomycin-p(A) expression cassette was purified and cloned into the compatible PvuII-BglII sites of pE3deltahyg to make plasmid pE3zeo.

This construct contained an Epstein Barr Virus (EBV) origin of replication (oriP), a eukaryotic selectable marker for zeocin resistance, a prokaryotic origin of replication (colE1), and a prokaryotic selectable marker (the β-lactamase gene conferring resistance to ampicillin). A reporter gene expression cassette was incorporated consisting of a tandemly duplicated set of response elements to confer responsiveness to signal transduction (cre elements), a minimal promoter that is recognizable by RNA transcription complex (containing at least a TATA box, a reporter gene (luciferase coding sequence), and the SV40 intervening sequence (IVS) and poly(A)+ signals).

The minimal promoter used was derived from the Herpes Virus thymidine kinase gene (available from vector pREP4, Invitrogen, nucleotides 2909 to 2667).

Construction of plasmids containing CC CKR2
pm3CCR2

The coding region for CC CKR2 was obtained by PCR amplification of genomic DNA using the following oligonucleotides:
sense: ccacaacatgctgtccacatctcgttc (SEQ ID NO:30)
antisense: cctctagagaccagccgagac (SEQ ID NO:31)

The PCR fragment was cloned directly into the StuI and XbaI sites of pm3ar and a clone with the correct sequence, plasmid (pm3arccr2), was used for further modification.

pm3CCR2sp

The hydrophobic signal sequence from pseudorabies virus gC protein was added to the CC CKR2 coding sequence by PCR as follows. Vector pm3arCCR2 was used as the template and oligos 54 (which begins at nt +153 and maps 3' to a convenient ApaI restriction site) and oligo 53 (which overlaps the CC CKR2 coding sequence and also contains a long tail encoding amino acids 9–23 of the hydrophobic signal sequence) were used as primers. The resulting 195 bp fragment was used as a PCR template with oligos 54 and oligo 52 (which encodes the remainder of the hydrophobic signal sequence, and contains a Kozak consensus sequence for efficient initiation of translation and an AgeI restriction site for subsequent cloning). The resulting 229 bp fragment was digested with AgeI and ApaI and cloned into the AgeI (in the multicloning site) and ApaI (found at nt +125 in the native human ccr2 gene) sites of pm3CCR2 to generate expression vector pm3CCR2sp.

Oligos used in the amplification of the human CC CKR2 coding sequence were as follows:

52. taaccggtcaccATGGCTTCCCTG-GCTCGTGCGATGCTGGCTCTGCTG-GCTCTGTACGC (SEQ ID NO:32)
53. CTGGCTCTGCTGGCTCTGTACGCTGCT-GCTATCGCTGCTGCTCCActgtccacatctcgttctcgg (SEQ ID NO:33)
54. ccagcgagtagagcggaggc (SEQ ID NO:34)

EXAMPLE 2
Production of Stably Transfected Cell Lines Using Two Episomes Transfection methods 293 cells were tranfected using the calcium phosphate procedure as described in Sambrook, J., Fritsch, E. F., and Maniatis, T. (1989) "Molecular Cloning: A Laboratory Manual," Cold Spring Harbor Laboratory Press, Cold Spring Harbor, N.Y., pp 16.33–34.

Briefly, 4 to 20 μg of transfection plasmid DNA was prepared per T75 flask of 293 cells. Each T75 flask contained from 0.75 to 1.5×10$^6$ cells and 10 to 12 mL of DMEM media supplemented with 10% fetal bovine serum (FBS). The DNA and 62.5 μL of 2 M CaCl$_2$ were added to H$_2$O to make 500 μL of solution per flask. To this solution was added 500 μL of HEPES-buffered saline (HBS) and the entire 1.0 mL of solution was added directly to the T75 culture medium. The transfection mix was allowed to incubate on the cells for 24 to 48 hrs at which time the cells were washed 1× or 2× with PBS and refed selective media (DMEM, 10% FBS, with or without gentamycin or penstrep, and supplemented with 1 μg/mL, puromycin and/or 250 μg/mL hygromycin). Selective media was changed every 3 to 5 days until cells approached confluence at which time cells were diluted at ratios between 1 to 4 and 1 to 50 in fresh selective media as needed.

Results

Plasmids pE3orl1 or pm3CCR3sp encoding the G protein coupled receptors orphanin (or 1.1 or nociceptin receptor, Noci) and CC chemokine CCR3, respectively, were transfected into 293E cells and selected with hygromycin (Hyg). This resulted in cell line 293no expressing the orphanin receptor and cell line 293c3 expressing CCR3. After 1 week in culture, plasmid pE3purGiα2 encoding the G protein inhibitory alpha subunit 2 (Gi), or the parental empty puromycin vector pE3pur (empty vector) was transfected into each of the two receptor expressing cell lines to produce the following four cell lines: 293noiHP (Noci+Gi, Hyg and Pur resistant); 293noHP (Noci+empty vector, Hyg and Pur resistant); 293c3iHP (CCR3+Gi, Hyg and Pur resistant); and 293c3HP (CCR3+empty vector, Hyg and Pur resistant), respectively. Selective pressure was maintained for 5 months during which time the stability of the dually expressing episomal lines was assessed by determining receptor Kd and Bmax, calcium mobilization assays, and northern blot analysis.

Results—calcium mobilization

Figure 14A:
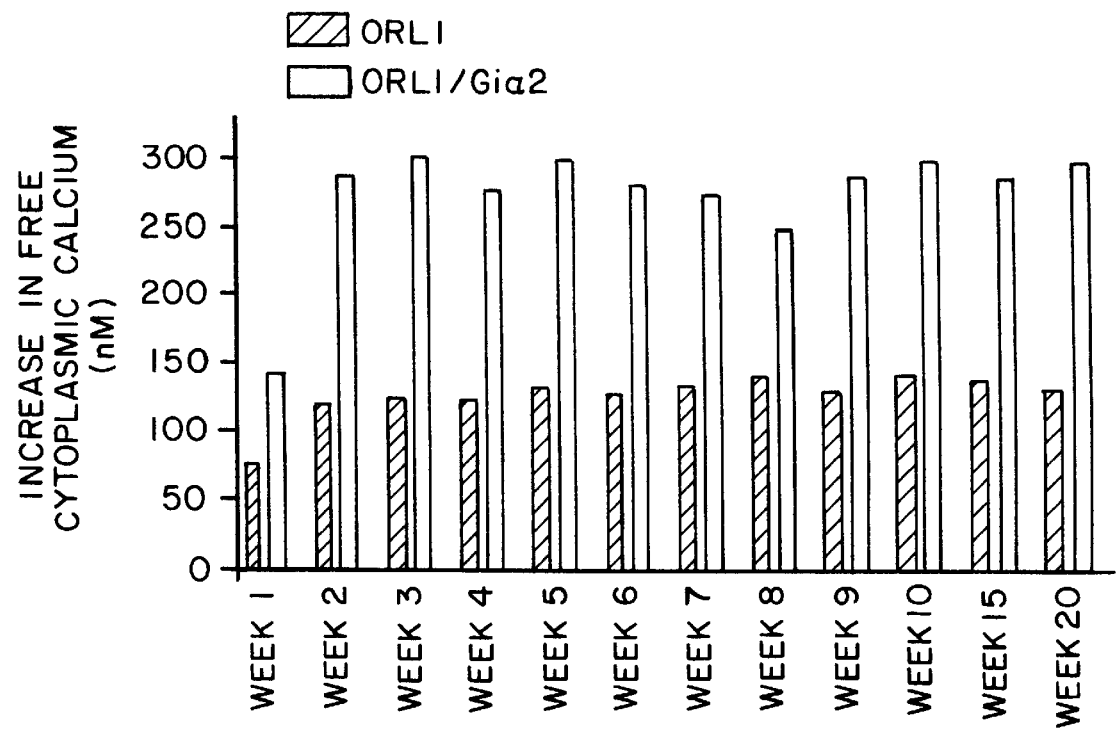
FIGS. 14a and 14b are graphs showing the increase in free cytoplasmic calcium over time in cells transfected with ORL1/Giα2(a) or SP CCR3/Giα2(b).
Figure 14B:
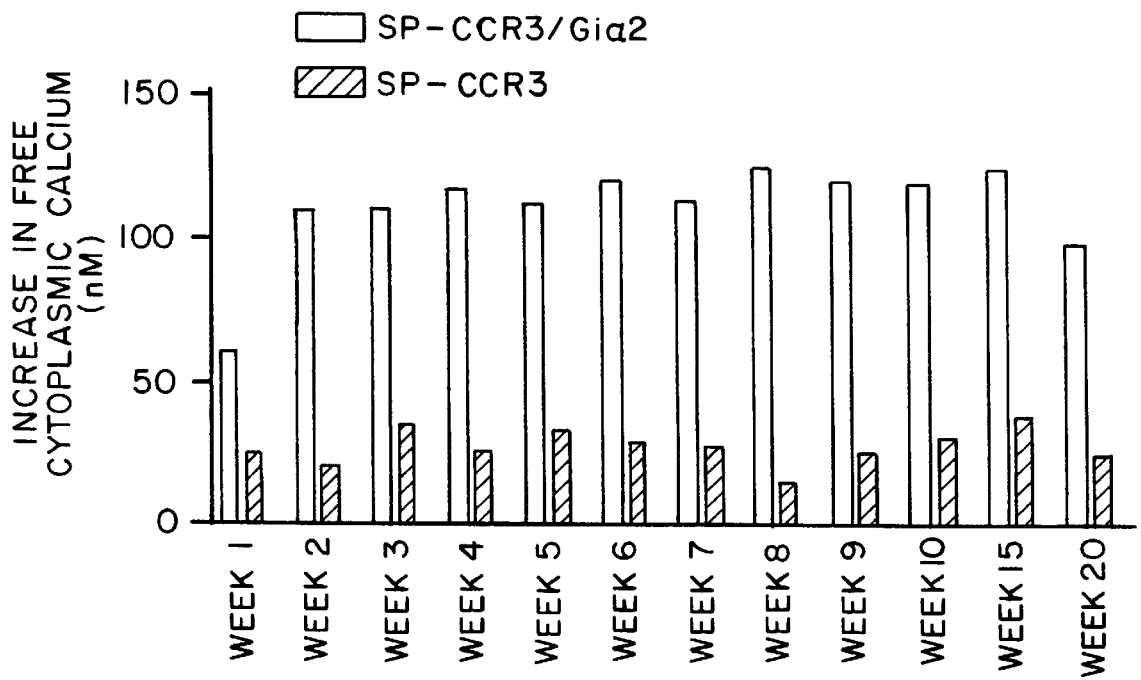

The increase in free cytoplasmic calcium in response to addition of receptor ligand (nociceptin and eotaxin for orl-1 and CCR3, respectively) was assayed weekly for 10 weeks, then at 5 week intervals after week 10. Results indicate that the addition of the second, G protein expressing episome significantly magnified the calcium mobilization signal for each receptor (~2.25× and 4× for orl1 and CCR3, respectively). Furthermore, the increased signal was stable by the second week after transfection and did not significantly change for any of the four cell lines at any point during the 20 week experiment (FIG. 14). These results were extended to a 6 month time point and no change in calcium signal was found (data not shown).

Results—Receptor Binding

Receptor $B_{MAX}$ and $K_D$ were determined for the 293E lines expressing CCR3 with or without G$\alpha$i2 (cell lines 293c3, 293c3iHP) and CXCR2 with or without G$\alpha$i2, (cell lines 293x2, and 293x2iHP), respectively (See Table I).

TABLE I

| RECEPTOR NAME | $K_D$(nM) | RECEPTOR # (1000) | STAGE |
| --- | --- | --- | --- |
| SP-CCR3 | 0.25 | 21 | MONTH 1 |
| SP-CCR3 | 0.19 | 19 | MONTH 5 |
| SP-CCR3/Gi | 0.19 | 23 | MONTH 1 |
| SP-CCR3/Gi | 0.18 | 21 | MONTH 6 |
| CXCR2 | 2 | 500 | MONTH 1 |
| CXCR2 | 2.8 | 500 | MONTH 2 |
| CXCR2/Gi | 1.4 | 550 | MONTH 1 |
| CXCR2/Gi | 1.9 | 500 | MONTH 2 |

In Table I, "SP-CCR3" refers to expression of the CCR3 receptor alone. "SP-CCR3/Gi" refers to expression of the CCR3 receptor and the G$\alpha$i2 subunit. "CXCR2" refers to expression of the CXCR2 receptor alone. "CXCR2/G" refers to expression of the CXCR2 receptor in combination with the G$\alpha$i2 subunit.

Figure 15A:
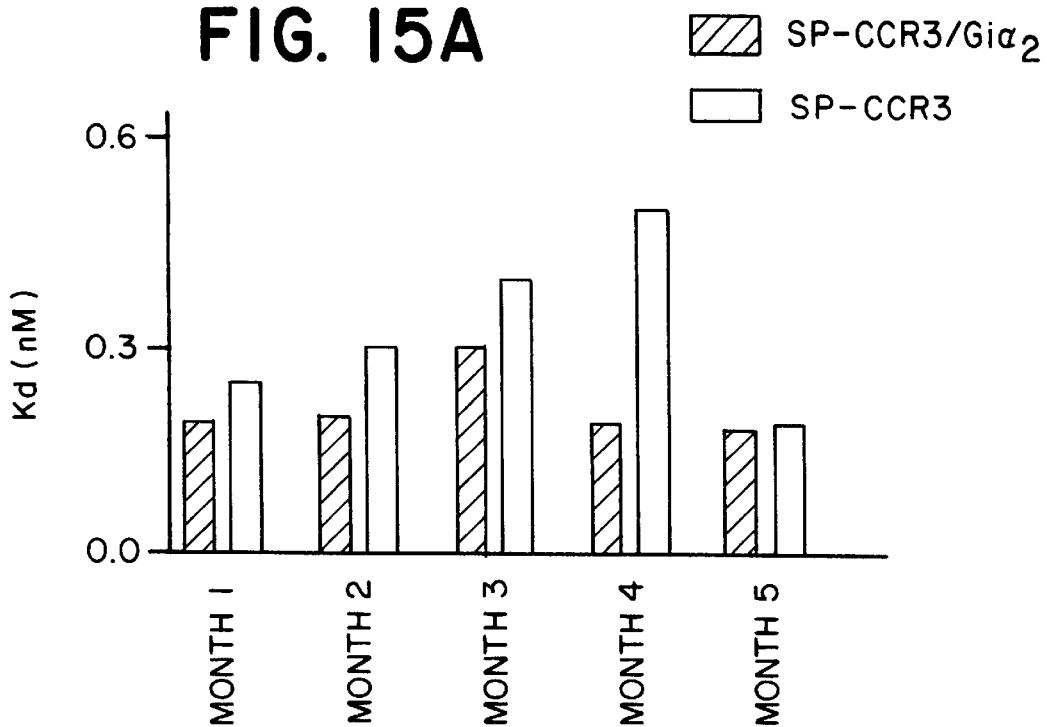
FIG. 15 shows graphs depicting Kd and Bmax, for cells expressing CCR3 and the combination of CCR3 and Giα2 over time.
Figure 15B:
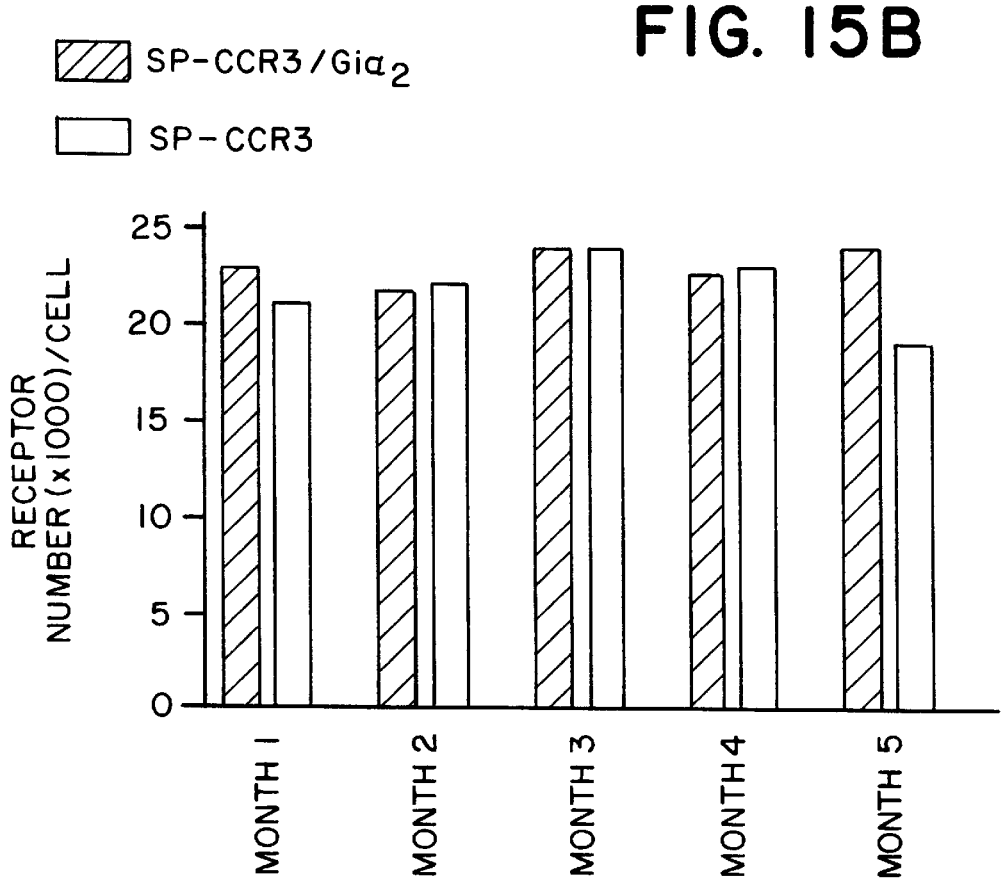

These results indicate that there is a $B_{max}$ of 19,000 to 23,000 receptors per cell and $K_D$ values that are not significantly different regardless of the presence of a second (i.e. Gi-expressing) episome, and regardless of the age of the cell line (month 1 and month 5 give the same $B_{max}$). Shown in FIG. 15 is a more detailed examination of $B_{max}$ and $K_D$ results for cell lines 293c3 ("SP-CCR3")and 293c3iHP ("SP-CCR3/G$\alpha$i2") demonstrating that the expression of receptors is stable at least from month 1 to month 5. This indicates that the presence of a second episome does not interfere with the expression of the receptor from the first episome as measured by $B_{max}$ and $K_D$ characteristics.

Results—Northern blot analysis

Figure 17A:
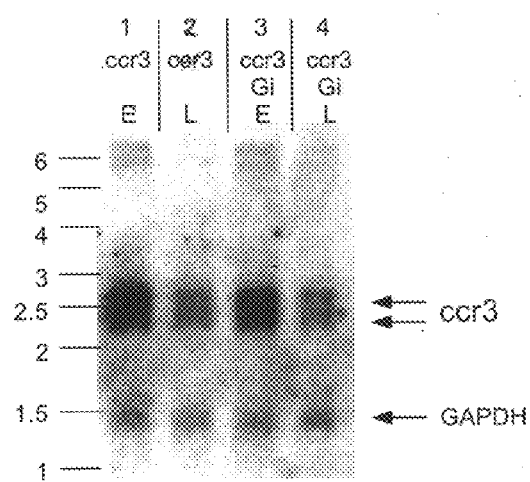
FIGS. 17A and 17B are Northern blot analyses of RNA isolated from early and late passage 293C3 and 293C3. HP cells probed with CCR3 (a) or Giα2 (b).
Figure 17B:
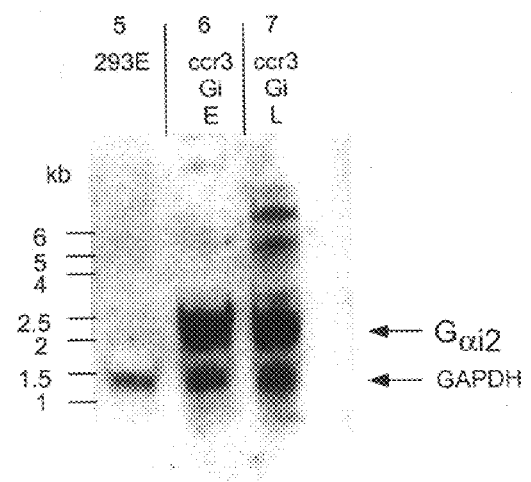

Total RNA was isolated from early (4 weeks after final transfection) and late (4 months after final transfection) cells as follows: 293no (expressing orl1), 293noiHP (expressing orl1 and G$\alpha$i2). 293c3 (expressing ccr3), and 293c3iHP (expressing ccr3 and G$\alpha$i2). RNA was run on denaturing formaldehyde gel (Sambrook et al.) and probed for orl1 or G$\alpha$i2 (FIG. 16) or ccr3 or G$\alpha$i2 (FIG. 17). For the northern blots shown in FIGS. 16 and 17, an equimolar amount of probe for the highly expressed housekeeping gene, GAPDH, was concomitantly added to the hybridization mix for normalization purposes. The arrows are labeled as appropriate and point to the recombinant G$\alpha$i2 mRNA (visible in FIG. 16, lanes 1 and 2; and in FIG. 17, lanes 6 and 7); to the recombinant orl1 mRNA (visible in FIG. 16, lanes 6–9); to the recombinant ccr3 mRNA (visible in FIG. 17, lanes 1–4); and to the native cellular GAPDH mRNA (visible in FIGS. 16 and 17, all lanes).

In FIG. 17, RNA was run on denaturing formaldehyde gel (Sambrook et al., 1989) and probed for ccr3 and GAPDH (panel A) or G$\alpha$2 and GAPDH (panel B). Probes for ccr3, G$\alpha$2 and GAPDH were approximately 500 bp in length (derived only from coding sequences) and were biotinylated using the BrightStar kit from Ambion, Inc., Austin, Tex. Equimolar concentrations of probe for the highly expressed housekeeping gene, GAPDH, was concomitantly added to the hybridization mix for normalization purposes. (Each probe was used at a concentration of approximately 0.1 nM.) Blot was hybridized overnight at 42° C. in 5× SSC, 50% formamide, 2× Denhardts, 0.2% SDS. Blot was then washed for 2× 15 min. in 0.2× SSC, 0.2% SDS at 50° C. Blot was developed as per protocol provided by Ambion and exposed to film for approximately 1 hour.

The arrows are labeled as appropriate and point to the two recombinant ccr3 mRNA species (Panel A); to the recombinant G$\alpha$2 mRNA (panel B); and to the native cellular GAPDH mRNA (Panels A and B). The nature of the differences between the two forms of ccr3 mRNA is unknown but may be due to incomplete splicing of the SV40 IVS, or to different sites of poly(A) addition.

This experiment shows that transcription from a second episome (E3purG$\alpha$i2) does not significantly affect transcription from an already resident episome (pE3orl1, FIG. 16; pm3ccr3sp, FIG. 17) since steady-state mRNA levels are only weakly, if at all, perturbed (compare FIG. 16, lanes 6 with 8, and 7 with 9; or FIG. 17, lanes 1 with 3, and 2 with 4). Furthermore, these experiments show that this observation could be replicated using at least two different types of receptors.

Construction of pm3orl1

The 1110 bp coding sequence for human orphanin receptor type I (orl1) was PCR amplified from whole human brain Quickclone cDNA (Clontech) using the following oligos:

Orl 1. CCCTCTAGACC ATGGAGCCCCTCTTCCCCGCGCCG (SEQ ID NO:35)

Orl 2. CCCTCTAGACCAGGCACCATGGGCAG-GTCCACGC<u>C</u> (SEQ ID NO:36)

The ATG start codon is underlined in orl 1, and the underlined C in orl 2 is *G* of TAG stop codon when looking at reverse complement. Each oligo contains an NcoI site.

The PCR product was digested with NcoI and cloned into the NcoI site of Litmus 28 (New England BioLabs, Beverly, Mass.). The fragment containing the orl1 coding sequence was then reclaimed from Litmus 28 with AgeI (5' side) and XhoI (3' side) and the resulting 1200 bp fragment was cloned into the AgeI and XhoI sites of vector pE3 (FIG. 11) to make pm3orl1.

TABLE II

| SAMPLE | ORL1/GAPDH ratio |
| --- | --- |
| orl1 + Gi early | 0.68 |
| orl1 + Gi late | 0.81 |
| orl1 + pEpur early | 0.85 |
| orl1 + pEpur late | 1.06 |
| | Gi$\alpha$2/GAPDH ratio |
| orl1 + Gi early | 1.60 |
| orl1 + Gi late | 1.26 |

As shown in Table II, the ratio of orl 1 to GAPDH RNA tended to increase as the cells aged: from 0.68 (early) to 0.81 (late) for 293noiHP cells and from 0.85 (early) to 1.06 (late) for 293no cells. Conversely, the ratio of Gi to GAPDH RNA decreased from 1.60 to 1.26 in the 3 month interval between the early and late RNA harvests. This may indicate an overall balancing trend in this particular example over time in which RNA concentrations from both expression cassettes tend toward a 1:1 steady-state ratio with each other.

Western blot analysis of Gαi2 expression

Figure 18:
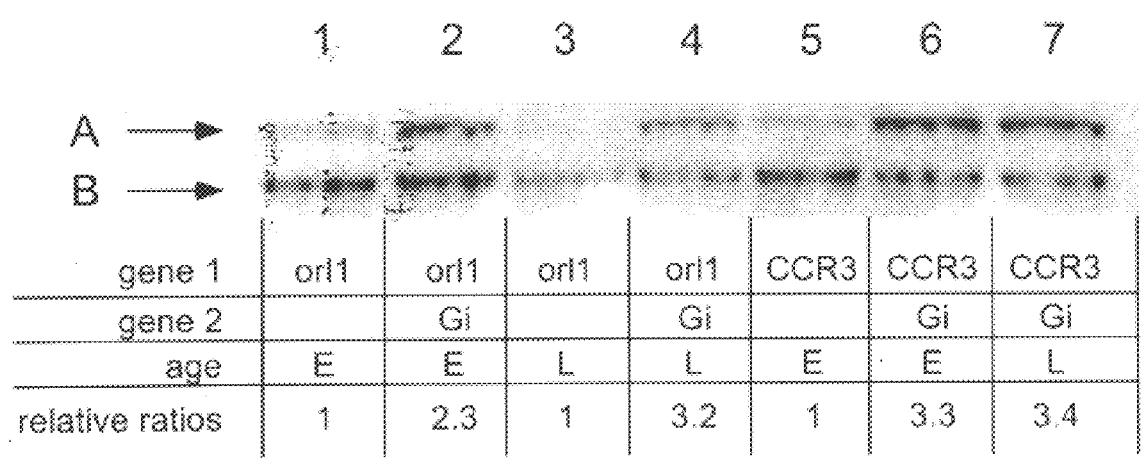
FIG. 18 is Western blot analysis of Giα/ORL1 or CCR3 expression.

It is well-known that the steady-state concentration of mRNA in a cell does not necessarily correlate with the steady-state level of protein present in the same cell. Therefore the presence of a greatly increased concentration of Gαi2 mRNA does not necessarily indicate a similar rise in intracellular Gαi2 protein concentration. The presence of Gαi2 was therefore measured using western blot analysis. An antibody directed against Gαi2 was used to probe a blot containing extracts from 293no, 29αnoiHP, 293c3, and 293c3iHP cells. Results from the western blot analysis (FIG. 18) indicated that a small amount of Gi was endogenously expressed in 293E cells (lanes 1, 3 and 5). Transfection of pE3purGiα2 was able to augment Gi concentrations by 2.2- to 3.4-fold in the stable cell lines (lanes 2, 4, 6 and 7). The autochemiluminograph was scanned as described for the northern blot above. In this Figure, the band marked "A" marks the position of Gαi2 protein, and the band "B" marks a constitutive, non-specific, cross-reactive protein.

Genomic Southern analysis

Figure 19:
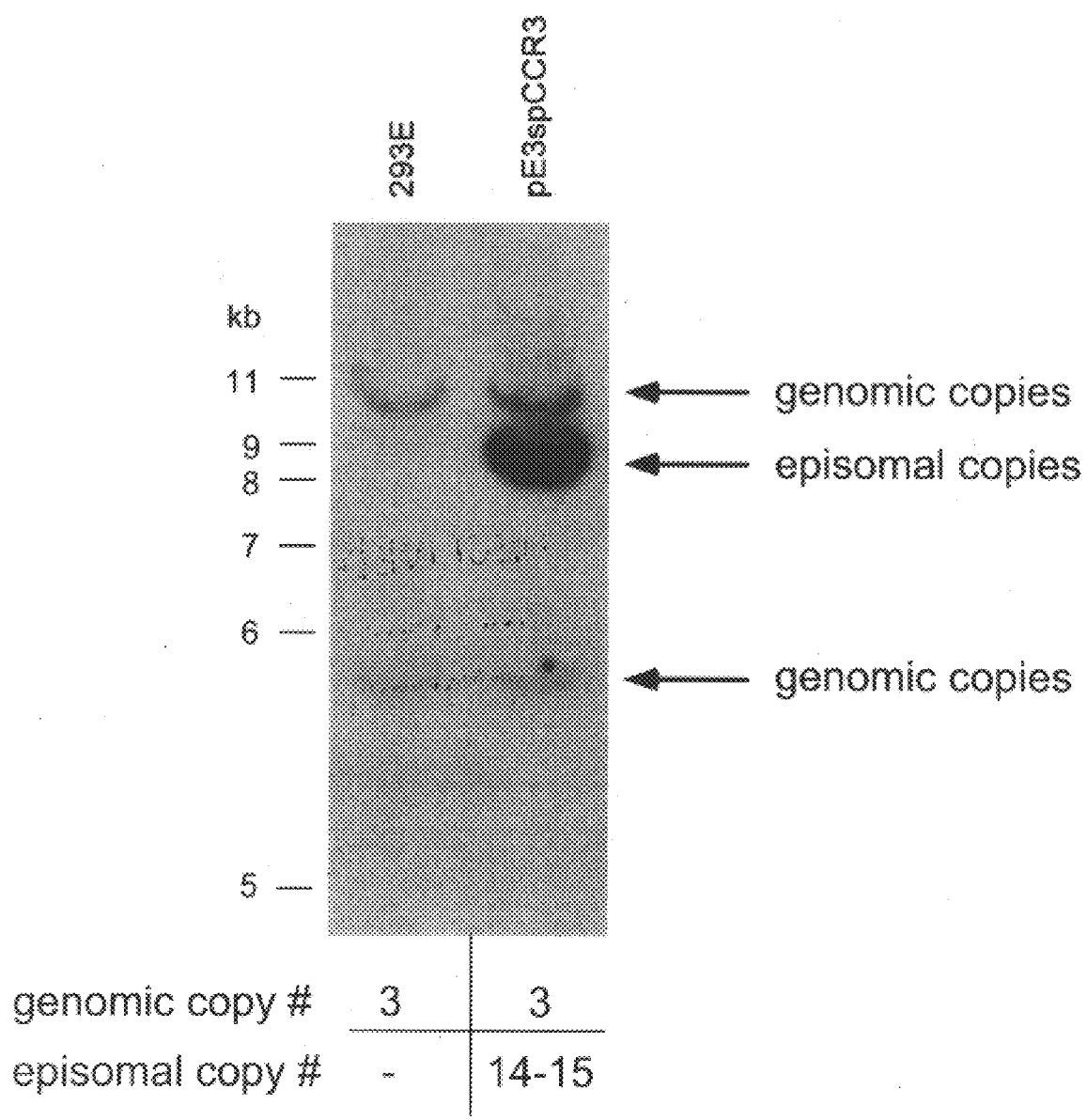
FIG. 19 is a Southern blot analysis of DNA isolated from 293c3 and 293c3HP cells.
Figure 20:
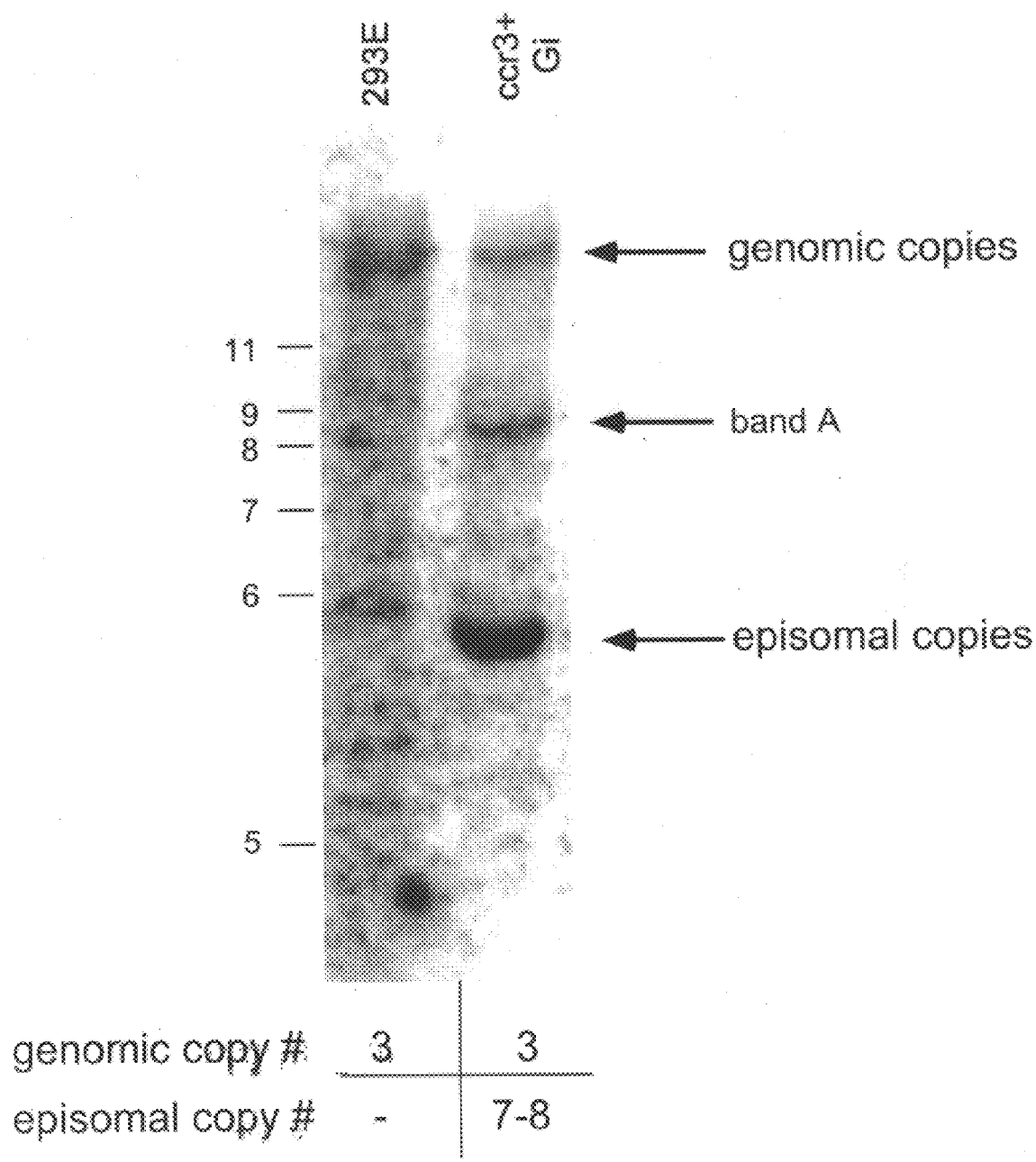
FIG. 20 is Southern blot analysis of DNA isolated from HEK 293 cells.

DNA was isolated from 293c3 and 293c3iHP cells at 5 weeks following the final transfection. DNA was digested overnight with XbaI, run on a 0.8% agarose gel, and the blot was transferred in 0.4 M NaOH to a positively charged nylon membrane (Boehringer Mannheim). Probes used in this experiment were a 428 bp fragment from the CCR3SP coding region (representing amino acids 85 through 227), and a 330 bp fragment from the Gαi2 coding region (representing amino acids 1 through 110). Blots were incubated with 20 ng/mL of probe at 42° C. in hybridization buffer (Dig EasyHyb Buffer, Boebringer Mannheim) as described in Horlick et al., (*Prot. Exp. And. Purific.* 9:301–308, 1997) overnight, washed 2× in 0.2× SSC, 0.1% SDS at 55° C. and developed using Boehringer Mannheim's Genius kit according to the supplied protocol. The genomic copies of CCR3 are visible at 10.5 kb and 5.8 kb (FIG. 19) while the episomal copies of CCR3 (plasmid pE3spCCR3) are visible as expected at 9 kb. For purposes of this experiment, the episomal band at 9 kb was compared to the genomic band at 10.5 kb. (CCR3 is not known to be present in the genome at multiple loci, therefore the weakly hybridizing genomic band migrating at 5.8 kb may represent a ccr3 pseudogene or other gene containing some homology with ccr3.) The value obtained for background intensity (region of the film not containing any bands) was subtracted from both episomal and genomic band values. Results indicated that the intensity of the episomal band was approximately 5-fold greater than that for the genomic band. Since it is known that HEK293 cells are hypotriploid with a modal chromosome number of 64 (Graham et al. 5. *J Gen Virol.* 36: 59–74, 1977; Hay et al. in ATCC: Catalogue of Cell Lines and Hybridomas, 7th ed., American Type Culture Collection, Rockville, Md., p.148, 1992), multiplying the relative intensity values by 3 provides the copy number per cell (Horlick et al., 1997). Thus, there were 14–15 copies of CCR3 per cell. In FIG. 20, the genomic copy of Gαi2 migrated at 13–14 kb, while the episomal band migrated at 5.8 kb. The band migrating in the CCR3+Gi lane at 8.8 kb (band A) may represent a small amount of XbaI partially cut, linearized episome. The intensity of the episomal Gi band at 5.8 kb was ~2.4-fold as intense as the genomic copy, indicating the presence of approximately 7–8 copies of the Gi episome per cell (FIG. 20).

Conclusions

The results presented here demonstrated that eukaryotic cell lines transfected according to the present invention stably harbor two episomes for long periods of time. In the examples above, addition of a second episome did not interfere with expression from either episome, as gauged by the following observations:

1. There was no change in receptor Bmax or KD whether the cells contain 1 or 2 episomes (CCR3±Gαi2 results)
2. Once expression had stabilized at week 2, there was no further change in agonist induced calcium mobilization signal, even after 20 weeks in culture. This was true for both single and doubly transfected cells (i.e., the CCR3±Gαi2; and orl1±Gαi2 results).
3. Addition of 2.3 to 3.4-fold more Gαi2 (western blot results, FIG. 18) augmented the calcium signal by 2.25-fold and 4-fold for orl1 and ccr3, respectively (FIG. 18).
4. Levels of expression of recombinant RNA from each episomal CMV promoter was of approximately the same magnitude as for the highly abundant housekeeping gene GAPDH, regardless of whether a second episome was present. Since GAPDH in one of the most abundant RNA species in the cell and represents approximately 0.8 to 3.6% of poly($A^+$) transcribed (Piechaczyk et al., *Nucleic Acids Res.* 12: 6951–6963, 1984; Horlick et al., 1997, supra), the amount of recombinant RNA transcribed for each episome was extremely high (FIG. 17).
5. There were approximately 14–15 copies of the CCR3 encoding episome per cell and approximately 7–8 copies of the Gi encoding episome per cell. Therefore, the presence of both episomes could be detected by genomic southern blotting in copy numbers consistent with the amounts detected for transfection of single episomes by Horlick et al., 1997, supra; Sugden et al., *Mol Cell Biol.* 5: 410–413, 1985; Yates et al., *Proc. Nat. Acad. Sci. USA* 81: 3806–3810, 1984.

EXAMPLE 3

Triple episomal lines

In addition to cell lines stably harboring two episomes, transfection and maintenance of higher numbers of episomes in 293E cells has also proven successful. For the experiments described below, an episome containing the coding sequence of a receptor (orl1) and the hygromycin resistance marker, an episome containing the coding sequence of Gαi2 and the puromycin resistance marker, and an episome containing the coding sequence of a luciferase (luc) and the zeocin resistance marker were transfered into 293E cells. Transcription of the luc coding sequence was placed under the control of cyclic AMP (cAMP) response elements (cre).

The design of the experiment was as follows:

1. Addition of forskolin to the cell line stimulates adenylyl cyclase activity resulting in an increase in intracellular cAMP concentration. The rise in cAMP concentration causes increased transcription of a luc reporter gene via adjacent cre elements, and ultimately, an increase in luc protein concentration and activity.
2. Addition of a Gαi2-coupled hormone receptor agonist to the cell line inhibits forskolin induced adenylyl cyclase activity, thus inhibiting transcription of the luc gene (and therefore, luc protein activity) to low levels.
3. Addition of a Gαi2-coupled hormone receptor antagonist to (2) above reverses the agonist-induced inhibition (termed "disinhibition") of adenylyl cyclase leading to an increase in luc activity greater than in the presence of forskolin+agonist, but not necessarily as great as in the presence of forskolin alone.

With the three episomes, stable cell lines were generated that 1. express high levels of cell surface receptors;
2. respond to transient changes in intracellular cAMP concentrations by modulating transcription of a reporter gene (luc); and
3. significantly increase the magnitude of the response described in (2) above due to the presence of an increased concentration of the G protein subunit, $G\alpha i2$.

Luciferase assays

In the first experiment, 293E cells were transfected with (orl1 and 6xcretkluc) ±$G\alpha i2$ to generate cell lines 293noilucHZ and 293noilucHPZ. (H=hygromycin resistant, P=puromycin resistant, Z=zeocin resistant.) In the second experiment, 293E cells were transfected with (spccr2 and luc) ±$G\alpha i2$ to generate cell lines 293r2lucHZ and 293r2ilucHPZ.

Luciferase protocol

Figure 21A:
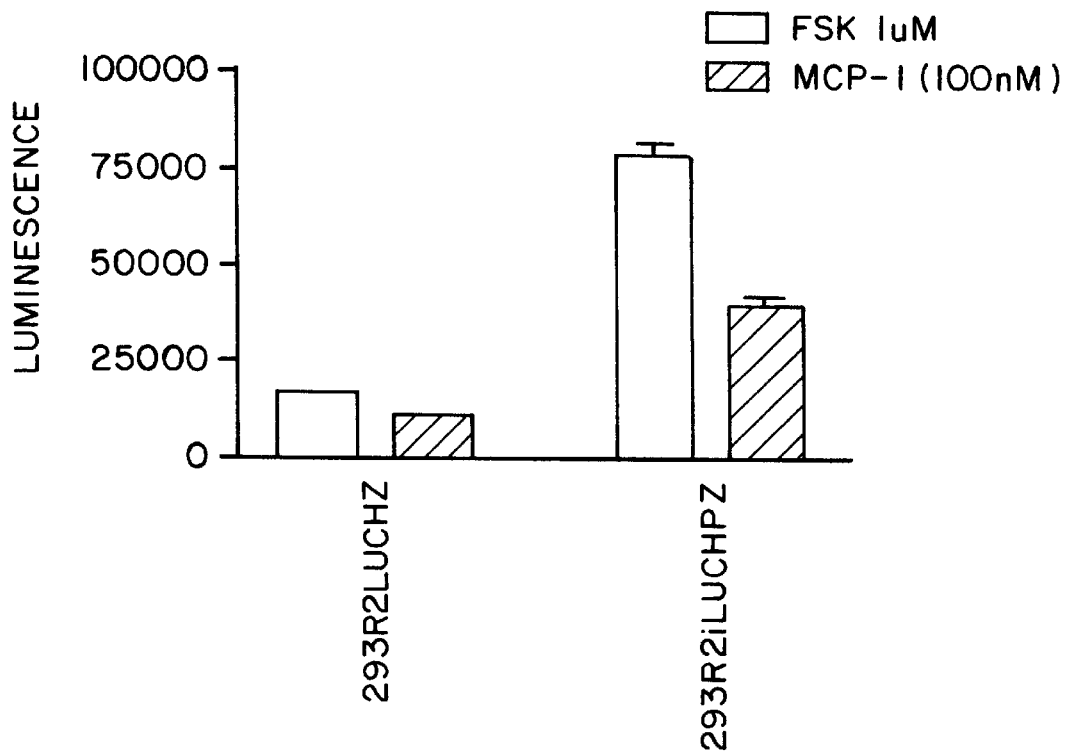
FIGS. 21a and 21b are graphs showing the inhibition of forskolin (FSK) induced luciferase expression in the presence of MCP-1(a) or nociceptin (NOCI) (b).
Figure 21B:
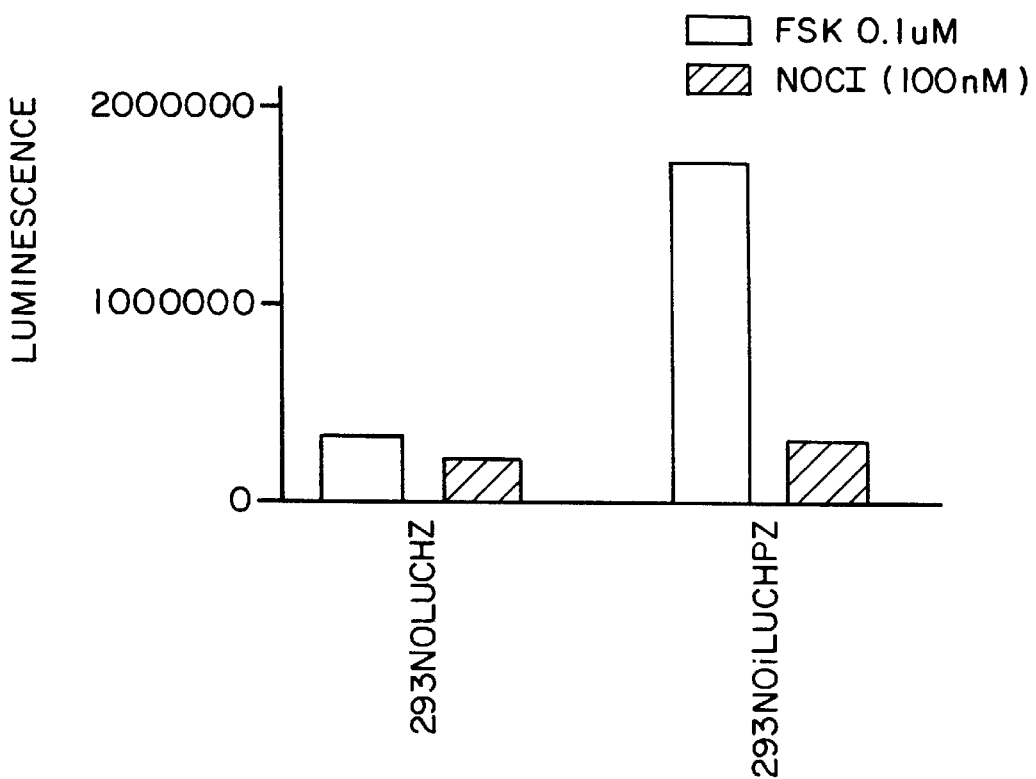

The experiment shown in FIG. 21 was obtained using 293nolucHZ, 293noilucHPZ, 293r2lucHZ and 293r2ilucflPZ cells after 4 months in culture (i.e., 4 months after transfection of the final episome). Cells were plated in 96-well format, 15,000 cells per well, in a 1:1 mixture of DMEM/F12 supplemented with 10% fetal calf serum, and appropriate selective antibiotics. After 18–24 hrs in culture, growth media was removed and 100 $\mu$L induction media was added. Induction media consists of Ultraculture (Biowhitakker, Walkersville, Md.)±1.0 or 0.1 $\mu$M forskolin (fsk) and ±100 nM nociceptin (noc) or 100 nM mcp-1, as shown in FIG. 21. Cells were incubated in induction media for 6 hrs., and media was then replaced with 50 $\mu$L of 1/1 mix of LucLite (Packard Instrument Co., Meriden, Conn.) and Hanks buffered saline solution, added directly to cells. Luminescence was detected using a Wallac Victor Luminometer.

Results in FIG. 21 show that addition of fsk caused an increase in luc activity (luminescence, in relative light units). In cell lines not co-transfected with Gi, the addition of ligand was able to suppress fsk induced luc activity by 25–30%. In cell lines co-transfected with Gi, the magnitude of ligand mediated suppression was increased to 50% and >80% for mcp-1 and noc, respectively. Furthermore, the presence of added Gi increased the overall fsk-induced signal by 4.6-fold and 5.7-fold (mcp-1 and noc stimulated cell lines, respectively). This experiment demonstrated the advantages of co-transfection of the third, G protein-containing episome into cell lines expressing both receptor and reporter genes.

Northern blot analysis

Figure 22A:
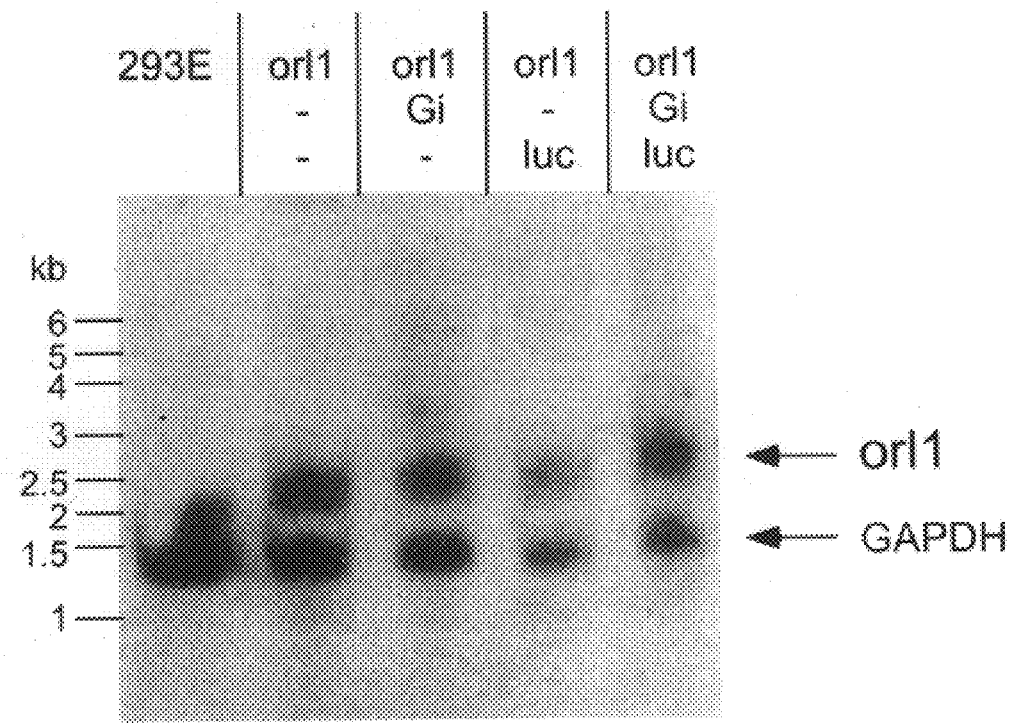
FIGS. 22a–22c are Northern Blot analyses of RNA isolated from cells transfected with ORL1, Giα2 or luc compared to GAPDH probed with ORL1 (a), Gαi2 (b), or luc (c).
Figure 22B:
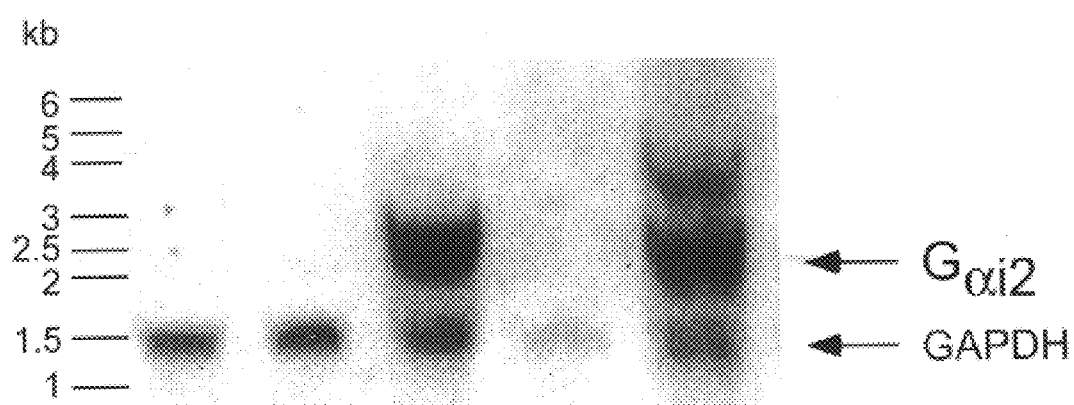
Figure 22C:
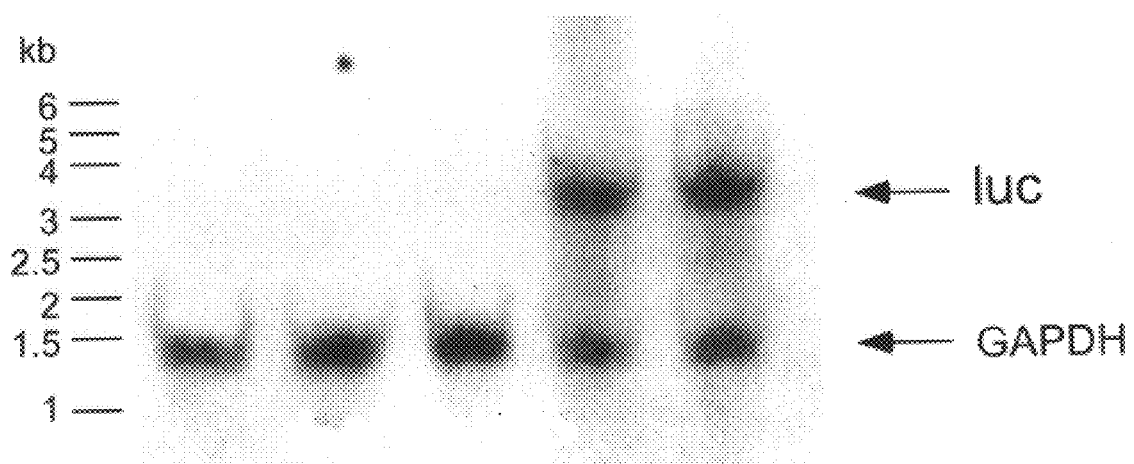

Total RNA was isolated from 293E cells (parental, untransfected cell line), and from 293no ("orl1,-,-"), 293noiHP ("orl1, Gi,-"), 293nolucHZ ("orl1,-, luc"), and 293noilucHPZ ("orl1, Gi, luc") cells 5–6 weeks following final transfection. 5 $\mu$g of RNA from each sample was run on a denaturing formaldehyde gel (Sambrook et al., 1989). The results shown in FIG. 22 indicate that the steady-state level of orl RNA was approximately 80% of the level of GAPDH (panel A), Gi RNA was present at 2- to 3-times the concentration of GAPDH (panel B), and luc (at uninduced levels) was present at an approximately equimolar ratio to that of GAPDH.

These experiments showed that levels of steady-state RNA derived from each of the three episomes was approximately the same magnitude as transcription of GAPDH, one of the most highly expressed genes of the cell (Piechaczyk et al., supra; Horlick et al., 1997, supra).

Genomic Southern blots

DNA was isolated from 293E cells (parental, untransfected cell line), and from 293no ("orl1,-,-" in FIG. 23), 293noiHP ("orl1, Gi,-"), 293nolucHZ ("orl1,-, luc"), and 293noilucHPZ ("orl1, Gi, luc") cells 5–6 weeks following final transfection. DNA was digested with HindIII, run on 0.8% agarose gel, processed, blotted, hybridized and probed as described above for "Results—Genomic southern analysis" in the "Results for dual expression system" section. Two probes were used concomitantly in this blot. The first consisted of a 498 bp fragment derived from the orl1 coding region, representing amino acids 134 to 301. This probe is specific for the genomic and episomal copies of orl1 and allows a direct comparison of relative intensity (and thus, cellular copy number) between the two. The second was a "universal probe" consisting of a 438 bp fragment derived from the amp gene that is common to all three of the episomes found within the orl1-expressing 293E cell lines and allows a direct comparison of copy number per cell among the three episomes.

Figure 23:
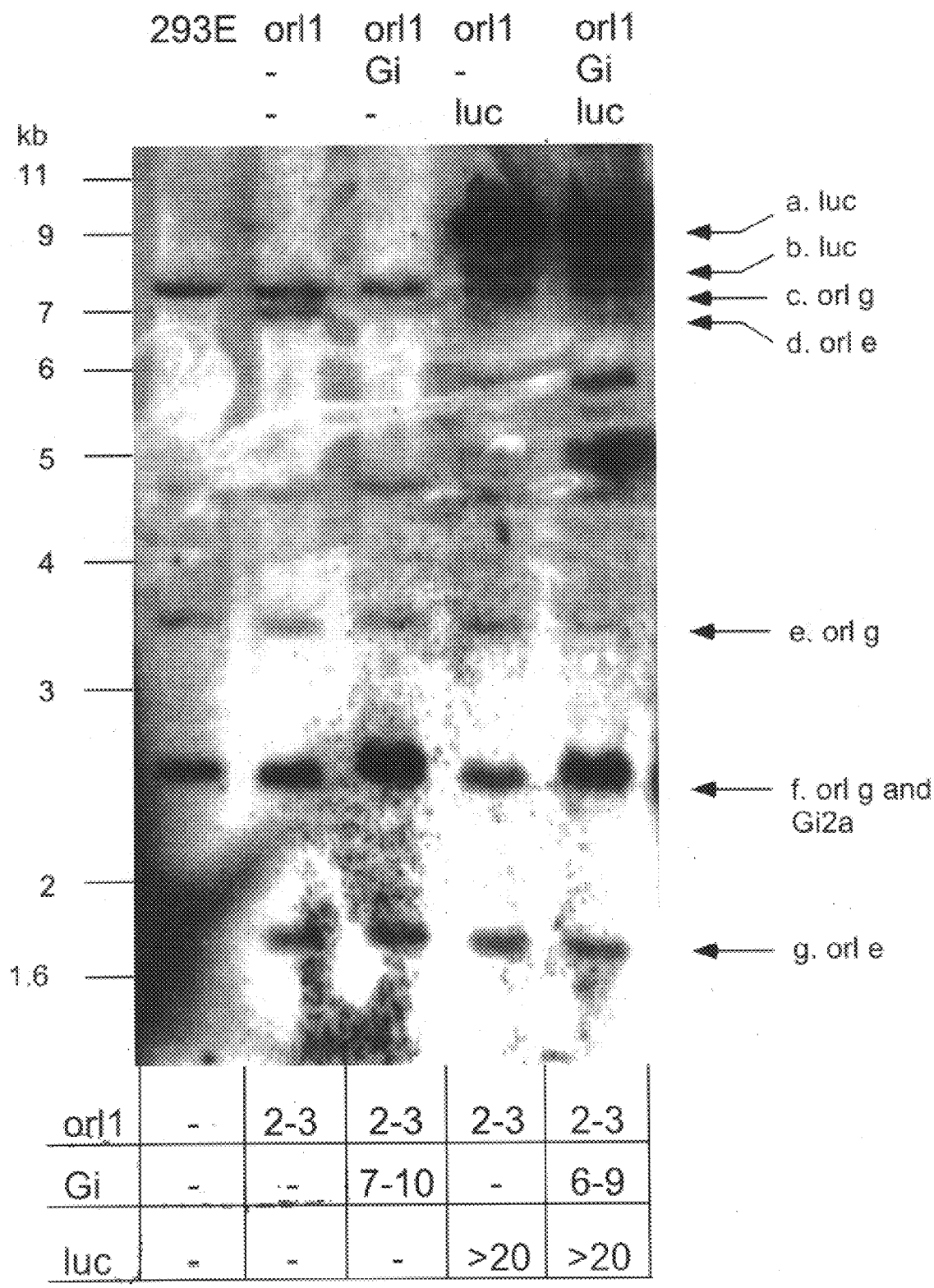
FIG. 23 is a genomic Southern blot analysis of DNA isolated from 293E, 293no, 293noiHP, 293nolucHP, 293lucHZ and 293noilucHPZ cells.

Genomic Southern blot results appear in FIG. 23. The designation 'g' or 'e' following orl indicates "genomic copy" or "episomal copy," respectively. Exposures of the blot on x-ray film (autochemilumiograph) for varying lengths of time were made for scanning purposes.

Number of pm3orl1 episomes per cell.

To determine the episome copy number for pm3orl1, the orl1 episomal band "g" was compared to the genomic band "c". Band c was chosen because its presence was not obscured as for band f. Band "e" is significantly fainter than band c and may represent a pseudogene or other related G protein coupled receptor gene. Since HEK293 cells are hypotriploid with a modal chromosome number of 64 (Graham et al., 1977; Hay et al., 1992), band "c" therefore most likely represents 3 copies. The intensity at "g" in each lane varies from 0.7 to 0.95 times the intensity measured for "c," leading to the calculation of 2 to 3 orl episome copies per cell.

Number of pE3purGi$\alpha$2 episomes per cell.

The episomal band derived from vector pE3purGi$\alpha$2 nearly co-migrates with one of the orl1 genomic bands (band "f"). Bands b and f are both visualized due to hybridization with the same "universal probe" described above. Therefore, to determine the episomal copy number for pE3purGi$\alpha$2, the average band intensity value derived from band f in the three non-Gi containing lanes was subtracted from the band f intensity obtained in lane (orl1,Gi,-) and lane (orl1,Gi,luc). This value was directly compared to the band intensity value derived from the orl1 episomal band b and led to the conclusion that there are 7–10 copies of pE3purGi$\alpha$2 per cell in the 293noiHP cell line, and 6–9 copies per cell in the 293noilucHPZ cell line.

Number of pE3zeocretkluc episomes per cell.

The main luc episomal band is represented by band "a." The nature of the slightly smaller, minor band "b" is unknown but may represent the migration on agarose of a small amount of single stranded plasmid, or a small population of rearranged vector. To calculate the number of pE3zeocretkluc per cell, the intensity of band "a" on a light autochemilumiograph exposure was compared to the intensities of the Gi component of band f. Results indicated that there were at least 20 copies of pE3zeocretkluc per cell in both the 293nolucHZ and 293noilucHPZ cell lines.

We claim:

1. A method for producing eukaryotic cells expressing two or more proteins from two or more transfected episomes which comprises:
   (i) transfecting eukaryotic host cells with (a) a first episome comprising an EBV origin of replication and a first gene encoding a protein of interest; and (b) a second episome comprising an EBV origin of replication and a second gene encoding a protein of interest, to produce transfected cells wherein said transfected cells express an EBNA 1 protein, wherein said first and second genes encode different proteins; and
   (ii) growing said transfected cells under conditions wherein said episomes express said first and second genes.

2. The method of claim 1 wherein said host cells constitutively expresses said EBNA 1 protein.

3. The method of claim 1 wherein said eukaryotic cells express EBNA 1 from a transfected episome.

4. The method of claim 1 wherein said first episome expresses said EBNA 1 protein in said transfected cells.

5. The method of claim 1 wherein said EBNA 1 protein comprises a truncated amino acid sequence of EBNA 1 effective to allow maintenance of said first and second episomes.

6. The method of claim 1 further comprising transfecting said host cell with a third episome comprising an EBV origin of replication and a third gene encoding a protein of interest and incubating said transfected host cell to express said third gene from said third episome.

7. The method of claim 1 wherein said first and second genes encode proteins selected from the group consisting of receptor proteins, transporter proteins, adhesion molecules, transcription factors and ion-channel proteins.

8. The method of claim 7 wherein said first gene encodes a receptor and said second gene encodes a signal transduction effector.

9. The method of claim 1 wherein said first and second genes are driven by strong promoters.

10. The method of claim 1 wherein said first and second episomes further comprise prokaryotic origins of replication.

11. The method of claim 1 wherein said first and second episome further comprise genes encoding prokaryotic selectable genetic markers.

12. The method of claim 11 wherein said prokaryotic markers are antibiotic resistance markers selected from the group consisting of ampicillin, tetracycline, chloramphenicol and kanamycin resistance markers.

13. The method of claim 1 wherein at least one of said episomes comprises a selectable marker for said host eukaryotic cells.

14. The method of claim 1 wherein said first and second episomes comprise selectable markers for said host eukaryotic cells.

15. The method of claim 14 wherein said selectable markers are different.

16. The method of claim 15 wherein said selectable markers for eukaryotic cells are selected from the group consisting of hygromycin, puromycin, gpt, neomycin, zeocin, ouabain, and blasticidin markers.

17. A method for producing a recombinant cell line expressing a plurality of proteins of interest comprising the steps of
   i) transfecting a first cell line with
      (a) a first episome which comprises an EBV origin of replication, a selectable genetic marker and a gene encoding an EBNA 1 protein;
      (b) a second episome comprising an EBV origin of replication, a gene encoding a first protein of interest and a first selectable marker for eukaryotic cells; and
      (c) a third episome comprising an EBV origin of replication, a second protein of interest and a second selectable genetic marker for eukaryotic cells, thereby producing a transfected cell line,
   ii) incubating the transfected cells in media wherein only cells expressing said EBNA 1 and said first and second selectable markers grow and propagate, and
   iii) recovering transfected cells.

18. A recombinant eukaryotic cell stably transfected with first and second episomes, said first episome comprising an EBV origin of replication and a gene encoding a first protein; and said second episome comprising an EBV origin of replication, and a gene encoding a second protein, said recombinant eukaryotic cell expressing an EBNA 1 protein, wherein said genes encoding said first and second proteins are different.

19. A method for producing a recombinant eukaryotic cell line expressing proteins of interest, which comprises:
(i) transfecting a eukaryotic host cell line expressing an EBNA 1 protein with (a) a first episome which comprises an EBV origin of replication, a first selectable marker for said eukaryotic cell line, a procaryotic origin of replication, a first procaryotic selectable marker, and a first gene encoding a protein, said first gene being driven by a strong promoter; and (b) a second episome comprising an EBV origin of replication, a second selectable marker for said eukaryotic cell line, a procaryotic origin of replication, a second procaryotic selectable marker, and a second gene encoding a protein of interest, to produce stably transfected cells, wherein said first and second genes encode different proteins; and
(ii) incubating said transfected cells in medium wherein cells expressing said first and second selectable markers for said eukaryotic cell line survive for a time sufficient to allow cell propagation.

20. The method of claim 19 wherein said first and second selectable markers for said eukaryotic host cell line are different from each other.

21. A method for producing a recombinant eukaryotic cell line expressing a protein of interest, which comprises:
(i) transfecting a eukaryotic host cell line with (a) a first episome which comprises an EBV origin of replication, a procaryotic origin of replication, a gene encoding a procaryotic selectable marker, and a gene encoding an EBNA 1 protein; and (b) a second episome comprising an EBV origin of replication, a gene encoding a procaryotic selectable marker, a procaryotic origin of replication, a gene encoding a protein of interest, and gene encoding a selectable marker for said host cell line, to produce transfected cells; and
(ii) incubating said transfected cells in medium wherein only cells which express both said EBNA 1 protein and said selectable marker survive, for a time sufficient to allow cell propagation.

22. The method of claim 21 wherein said gene encoding an EBNA 1 protein and said gene encoding a protein of interest are driven by strong promoters.

23. The method of claim 21 wherein said procaryotic selectable markers are antibiotic resistance markers selected from the group consisting of ampicillin, chloramphenicol, tetracycline and kanamycin resistance markers.

24. The method of claim 21 wherein said first episome further comprises a selectable marker for said host eukaryotic cell line.

25. The method of claim 21 wherein said selectable genetic marker for eukaryotic cells is selected from the group consisting of hygromycin, neomycin, zeocin, gpt, ouabain, and blasticidin markers.

26. The method of claim 21 wherein said EBNA 1 protein is a truncated sequence of full-length EBNA 1 that is effective to allow maintenance of said second episome.

* * * * *